(12) United States Patent
Gong et al.

(10) Patent No.: US 10,196,613 B2
(45) Date of Patent: Feb. 5, 2019

(54) STEM CELLS FOR MODELING TYPE 2 DIABETES

(71) Applicant: Regeneron Pharmaceuticals, Inc., Tarrytown, NY (US)

(72) Inventors: Guochun Gong, Elmsford, NY (US); Ka-Man Venus Lai, Tarrytown, NY (US); David M. Valenzuela, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 45 days.

(21) Appl. No.: 14/974,785

(22) Filed: Dec. 18, 2015

(65) Prior Publication Data
US 2016/0177273 A1    Jun. 23, 2016

Related U.S. Application Data

(60) Provisional application No. 62/094,868, filed on Dec. 19, 2014.

(51) Int. Cl.
| | |
|---|---|
| *C12N 5/074* | (2010.01) |
| *A01K 67/027* | (2006.01) |
| *C12N 5/071* | (2010.01) |
| *G01N 33/50* | (2006.01) |
| *G01N 33/74* | (2006.01) |
| *A61K 35/39* | (2015.01) |
| *A61K 35/545* | (2015.01) |
| *C12N 15/10* | (2006.01) |
| *C12N 15/90* | (2006.01) |
| *C12N 15/11* | (2006.01) |

(52) U.S. Cl.
CPC ........ *C12N 5/0696* (2013.01); *A01K 67/0271* (2013.01); *A61K 35/39* (2013.01); *A61K 35/545* (2013.01); *C12N 5/0676* (2013.01); *C12N 5/0678* (2013.01); *C12N 15/102* (2013.01); *C12N 15/111* (2013.01); *C12N 15/90* (2013.01); *G01N 33/507* (2013.01); *G01N 33/5088* (2013.01); *G01N 33/74* (2013.01); *A01K 2207/12* (2013.01); *A01K 2227/105* (2013.01); *A01K 2267/0362* (2013.01); *C12N 2310/20* (2017.05); *C12N 2501/119* (2013.01); *C12N 2501/16* (2013.01); *C12N 2506/45* (2013.01); *G01N 2333/62* (2013.01)

(58) Field of Classification Search
CPC .................................................. C12N 5/0696
See application file for complete search history.

(56) References Cited

U.S. PATENT DOCUMENTS

| | | |
|---|---|---|
| 2014/0242038 A1 | 8/2014 | Hua et al. |
| 2015/0218522 A1 | 8/2015 | Peterson et al. |
| 2016/0177273 A1 | 6/2016 | Gong et al. |

FOREIGN PATENT DOCUMENTS

| | | |
|---|---|---|
| WO | WO 2008/096009 A2 | 8/2008 |
| WO | WO 2014/201167 A1 | 12/2014 |
| WO | WO 2015/089462 A1 | 6/2015 |
| WO | WO 2016/100857 A1 | 6/2016 |

OTHER PUBLICATIONS

NCBI BLAST Printout Rattus norvegicus—3 pages.*
NCBI BLAST Printout Mus musculus—3 pages.*
Takahashi et al. (2007, Cell, vol. 131, pp. 861-872).*
Marx V. (2013, Cell Culture Technology, vol. 496, pp. 253-258).*
Bilic et al. (2012, Stem Cells, vol. 30, pp. 33-41).*
Cauchi, et al., "Meta-analysis and functional effects of the SLC30A8 rs13266634 polymorphism on isolated human pancreatic islets," Molecular Genetics and Metabolism, 100, 77-82 (2010).
Chimienti, et al., "Identification and Cloning of a β-Cell-Specific Zinc Transporter, ZnT-8, Localized Into Insulin Secretory Granules," Diabetes, vol. 53:2330-2337, (Sep. 2004).
D'Amour, et al., "Production of pancreatic hormone-expressing endocrine cells from human embryonic stem cells," Nature Biotechnology, vol. 24, No. 11, pp. 1392-1401 (Nov. 2006).
Davidson, et al., "Zinc Transporter 8 (ZNT8) and Beta Cell Function," Trends Endocrinol Metab, 25(8): 415-424 (Aug. 2014).
Flannick, et al.,"Loss-of-function mutations in SLC30A8 protect against type 2 diabetes," Nat Genet., 46(4):357-363, (Apr. 2014).
Hua, et al., "iPSC-derived β cells model diabetes due to glucokinase deficiency," Journal of Clinical Investigation, vol. 123, No. 7 pp. 3146-3153 (Jul. 2013).
Kawasaki, "ZnT2 and type 1 diabetes," Endocrine Journal, 59(7):531-537 (2012).
King, "The use of animal models in diabetes research," British Journal of Pharmacology, 166, pp. 877-894 (2012).
Knoepfler Lab Stem Blog, "Top 10 Takeaways from Harvard Stem Cell Diabetes Paper," retrived at: <http://www.ipscell.com/2014/10/> posted on Oct. 11, 2014.
Lemaire, et al., "Zinc transporters and their role in pancreatic β-cell," Journal of Diabetes Investigation, vol. 3, Issue 3, pp. 202-211 (Jun. 2012).
Merkle, et al., "Modeling Human Disease with Pluripotent Stem Cells: from Genome Association to Function," Cell Stem Cell, 12:656-668 (Jun. 6, 2013).

(Continued)

*Primary Examiner* — Thaian N Ton
*Assistant Examiner* — David A. Montanari
(74) *Attorney, Agent, or Firm* — Yongjin Choi; Alston & Bird LLP

(57) ABSTRACT

The invention provides stem cell derived beta-pancreatic cells and animal models of T2D in which cells have been grafted. The stem cells bear a mutated form of SLC30A8 conferring protection or susceptibility to T2D. The cells and animal models can be used for drug screening as well as to provide insights into the mechanism of T2D and potentially new therapeutic and diagnostic targets.

12 Claims, 5 Drawing Sheets

Specification includes a Sequence Listing.

(56) References Cited

OTHER PUBLICATIONS

Pagliuca, et al., "Generation of Functional Human Pancreatic β Cells in Vitro," Cell, 159:428-439 (Oct. 9, 2014).
Pagliuca, et al., "How to make a functional β-cell," Development, 140(12), pp. 2472-2383 (2013).
Rutter, "Think zinc, New roles for zinc in the control of insulin secretion," Islets, 2:1 49-50 (Jan./Feb. 2010).
'Rutter, et al., "SLC30A8 mutations in type 2 diabetes," Diabetologia, 58:31-36 (2015).
Shahjalal, et al., "Generation of insulin-producing β-like cells from human iPS cells in a defined and completely xeno-free culture system," Journal of Molecular Cell Biology Advanced Access, retrived from <http://jmcb.oxfordjournals.org. published Jun. 26, 2014.
Sladek, et al., "A genome-wide association study identifies novel risk loci for type 2 diabetes," Nature, vol. 445, pp. 881-885 (Feb. 22, 2007).
Tamaki, et al., "The diabetes-susceptible gene SLC30A8/Znt8 regulates hepatic insulin clearance," J. Clin Invest., 123(10):4513-4523 (2013).
Wijesekara, et al., "Beta cell-specific Znt8 deletion in mice causes marked defects in insulin processing, crystallisation and secretion," Diabetologia, 53:1656-1668 (2010).
Xavier, et al., "Animal Models of GWAS-Identified Type 2 Diabetes Genes," Journal of Diabetes Research, vol. 2013, Article ID 906590, 12 pages.
WIPO Application No. PCT/US2015/066757, PCT International Search Report and Written Opinion of the International Searching Authority dated Apr. 7, 2016.
Batista, et al., "Long Noncoding RNAs: Cellular Address Codes in Development and Disease," Cell, 152, pp. 1298-1307, (Mar. 14, 2013).
Bellomo, et al., "Zinc ions modulate protein tyrosine phosphatase 1B activity", Mellallomics, 6, pp. 1229-1239 (2014).
Dobson, et al., "The role of assembly in insulin's biosynthesis," Current Opinion in Structural Biology, 8, pp. 189-194, (1998).
Fukamachi, et al., "Zinc Suppresses Apoptosis of U937 Cells Induced by Hydrogen Peroxide through an Increase of the Bcl-2/Bax Ratio," Biochemicals and Biophysical Research Comm., 246, pp. 364-369, (1998).
Gerber, et al., "Hypoxia lowers SLC30A8/ZnT8 expression and free cytosolic Zn2+ in pancreatic beta cells," Diabetologia, 57, pp. 1635-1644, (2014).
Hardy, et al., "Effects of high-fat diet feeeding on Znt8-null mice: differences between β-cell and global knockout of Znt8," Am J Physiol Endocronol Metab, 302: E1084-E1096, (2012).
Kirchhoff, et al., "Polymorphisms in the TCF7L2, CDKAL1 and SLC30A8 genes are associated with impaired proinsulin conversion," Diabetologia, 51, pp. 597-601, (2008).
Lemaire, et al., "Insulin crystallization depends on zinc transporter ZnT8 expression, but is not required for normal glucose homeostasis in mice," PNAS, vol. 106, No. 35, pp. 14872-14877, (Sep. 1, 2009).
Loopstra-Masters, et al., "Proinsulin-to-C-peptide ratio versus proinsulin-to-insulin ration in the prediction of incident diabetes: the Insulin Resistance Atherosclerosis Study (IRAS)," Diabetologia, 54, pp. 3047-3054, (2011).
McCluskey, et al., "Development and Functional Characterization of Insulin-releasing Human Pancreatic Beta Cell Lines Produced by Electrofusion," The Journal of Biological Chemistry, vol. 286, No. 25, pp. 21982-21992, (Jun. 24, 2011).
Mitchell, et al., "Molecular Genetic Regulation of Slc30a8/ZnT8 Reveals a Positive Association With Glucose Tolerance," Mol Endocrinol, 30(1), pp. 77-91, (Jan. 2016).
Nicolson, et al., "Insulin Storage and Glucose Homeostasis in Mice Null for the Granule Zinc Transporter ZnT8 and Studies of the Type 2 Diabetes-Associated Variants," Diabetes, vol. 58, pp. 2070-2083, (Sep. 2009).
Pacini, et al., "Methods and Models for Metabolic Assessment in Mice," Journal of Diabetes Research, vol. 2013, Article ID 986906, 8 pages.
Pound, et al., "Deletion of the mouse Slc30a8 gene encoding zinc transporter-8 results in impaired insulin secretion," Biochem. J., 421, pp. 371-376, (2009).
Pound, et al., "The Physiological Effects of Deleting the Mouse Slc30a8 Gene Encoding Zinc Transporter-8 Are Influenced by Gender and Genetide Background," Plos one, vol. 7, Issue 7, e40972, (Jul. 2012).
Rutter, Conference on 'Diet, gene regulation and metabolic disease' Symposium 2: Micronutrients, phytochemicals, gene expression and metabolic disease intracellular zinc in insulin secretion and action: a determinant of diabetes rish?, Proceedings of the Nutrition Society,2016,vol. 75,pp. 62-72.
Saad, et al., "Disproportionately Elevated Proinsulin in Pima Indians with Noninsulin-Dependent Diabetes Mellitus," Journal of Clinical Endocrinology and Metabolism, vol. 70, No. 5, pp. 1247-1253, (1990).
Scharfmann, et al., "Development of a conditionally immortalized human pancreatic β cell line," The Journal of Clinical Investigation, vol. 124, No. 5, pp. 2085-2098, (May 2014).

* cited by examiner

Schematic of Cas9/sgRNA Construct

| Stage | Basal Media | Supplements | | |
|---|---|---|---|---|
| | | D'Amour (2006) | Hua (2013) | Kume (2014) |
| 1 Definitive Endoderm | RPMI | Activin A (100 ng/ml) Wnt3A (25 ng/ml) | Activin A (100 ng/ml) Wnt3A (25 ng/ml) EGTA (75uM) | Activin A (ng/ml) CHIR99021 2% B27 |
| 2 Primitive Gut Tube | RPMI | Activin A (100 ng/ml) 2%FBS | Activin A (100 ng/ml) 0.2%FBS | Activin A ng/ml 2% B27 |
| 3 Posterior Foregut | DMEM | FGF10 (50ng/ml) KAAD-cyclopamine (0.25 μM) 2%FBS | FGF10 (50ng/ml) KAAD-cyclopamine (0.25 μM) 2%FBS | FGF10 (ng/ml) KAAD-cyclopamine μM 1% B27 |
| 4 Pancreatic Endoderm | CMRL | FGF10 (50ng/ml) KAAD-cyclopamine (0.25 μM) Retinoic Acid (2uM) 1% B27 | FGF10 (50ng/ml) KAAD-cyclopamine (0.25 μM) Retinoic Acid (2uM) LDN 193189 (250 nM) B27 | NOGGIN (200-300ng/ml) KAAD-cyclopamine (μM) Retinoic Acid (μM) SB431542 nM 1% B27 |
| 5 Endocrine | CMRL | Exendin-4 (50 ng/ml) (+/-) DAPT 1% B27 (+/-) Exendin-4 (50 ng/ml) IGF1 HGF 1% B27 | Exendin-4 (50ng/ml) SB431542 (2 μM) B27 | Alk5i (5μM) ILV (300nM) NOGGIN (200ng/ml) 1% B27 Exendin-4 Nicotinamide (±) IBMX (±) FRKL 1% B27 |
| | | | B27 | |

FIG. 5

SEQUENCE LISTING

```
<160> NUMBER OF SEQ ID NOS: 14

<210> SEQ ID NO 1
<211> LENGTH: 80
<212> TYPE: RNA
<213> ORGANISM: Artificial sequence
<220> FEATURE:
<223> OTHER INFORMATION: Synthetic

<400> SEQUENCE: 1
guuuuagagc uagaaauagc aaguuaaaau aaggcuaguc cguuaucaac uugaaaaagu      60
ggcaccgagu cggugcuuuu                                                 80

<210> SEQ ID NO 2
<211> LENGTH: 42
<212> TYPE: RNA
<213> ORGANISM: Artificial sequence
<220> FEATURE:
<223> OTHER INFORMATION: Synthetic

<400> SEQUENCE: 2
guuuuagagc uagaaauagc aaguuaaaau aaggcuaguc cg                         42

<210> SEQ ID NO 3
<211> LENGTH: 30
<212> TYPE: RNA
<213> ORGANISM: Artificial sequence
<220> FEATURE:
<223> OTHER INFORMATION: Synthetic

<400> SEQUENCE: 3
guuuuagagc uagaaauagc aaguuaaaau                                      30

<210> SEQ ID NO 4
<211> LENGTH: 33
<212> TYPE: RNA
<213> ORGANISM: Artificial sequence
<220> FEATURE:
<223> OTHER INFORMATION: Synthetic

<400> SEQUENCE: 4
guuuuagagc uagaaauagc aaguuaaaau aag                                  33

<210> SEQ ID NO 5
<211> LENGTH: 26
<212> TYPE: RNA
<213> ORGANISM: Artificial sequence
<220> FEATURE:
<223> OTHER INFORMATION: Synthetic

<400> SEQUENCE: 5
gaguccgagc agaagaagaa guuuua                                          26

<210> SEQ ID NO 6
<211> LENGTH: 12
```

```
<212> TYPE: RNA
<213> ORGANISM: Artificial sequence
<220> FEATURE:
<223> OTHER INFORMATION: Synthetic

<400> SEQUENCE: 6
aaggcuaguc cg                                                          12

<210> SEQ ID NO 7
<211> LENGTH: 50
<212> TYPE: RNA
<213> ORGANISM: Artificial sequence
<220> FEATURE:
<223> OTHER INFORMATION: Synthetic

<400> SEQUENCE: 7
aaggcuaguc cguuaucaac uugaaaaagu ggcaccgagu cggugcuuuu                  50

<210> SEQ ID NO 8
<211> LENGTH: 23
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: n is a, c, g, or t

<400> SEQUENCE: 8
gnnnnnnnnn nnnnnnnnnn ngg                                              23

<210> SEQ ID NO 9
<211> LENGTH: 23
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(21)
<223> OTHER INFORMATION: n is a, c, g, or t

<400> SEQUENCE: 9
nnnnnnnnnn nnnnnnnnnn ngg                                              23

<210> SEQ ID NO 10
<211> LENGTH: 25
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(23)
<223> OTHER INFORMATION: n is a, c, g, or t

<400> SEQUENCE: 10
ggnnnnnnnn nnnnnnnnnn nnngg                                            25

<210> SEQ ID NO 11
<211> LENGTH: 21
<212> TYPE: DNA
<213> ORGANISM: Artificial sequence
<220> FEATURE:
<223> OTHER INFORMATION: Synthetic

<400> SEQUENCE: 11
```

```
gctctatgaa ccgtacctgc t                                               21

<210> SEQ ID NO 12
<211> LENGTH: 121
<212> TYPE: DNA
<213> ORGANISM: Artificial sequence
<220> FEATURE:
<223> OTHER INFORMATION: Synthetic

<400> SEQUENCE: 12
ttggtttgac tttgcagcac cagcctgctg ttattgctca ctctatgaac cgtacctgct     60
cagtgccatc caaatgtcag ccgcttagag ggaggcttcg atgacaacca cagggagaag    120
a                                                                    121

<210> SEQ ID NO 13
<211> LENGTH: 21
<212> TYPE: DNA
<213> ORGANISM: Artificial sequence
<220> FEATURE:
<223> OTHER INFORMATION: Synthetic

<400> SEQUENCE: 13
gaaccacttg gctgtcccgg c                                               21

<210> SEQ ID NO 14
<211> LENGTH: 121
<212> TYPE: DNA
<213> ORGANISM: Artificial sequence
<220> FEATURE:
<223> OTHER INFORMATION: Synthetic

<400> SEQUENCE: 14
gcatcgtaaa gcttttgcta agggctttag caatttctct ccgaaccact tggctgtccc     60
agctggctgc tgttgataaa gaagcacagg gagattagca ctgattgcac acgcatgggc    120
g                                                                    121
```

STEM CELLS FOR MODELING TYPE 2 DIABETES

CROSS REFERENCE TO RELATED APPLICATIONS

This application claims the benefit under 35 USC 119(e) of U.S. Provisional Application No. 62/094,868 filed Dec. 19, 2014, which is incorporated by reference in its entirety.

REFERENCE TO A SEQUENCE LISTING

This application incorporates by reference the Sequence Listing submitted in Computer Readable Form as file 471380SEQLST.txt, created on Dec. 18, 2015, and containing 3,406 bytes.

BACKGROUND

Diabetes is a disorder characterized by metabolic defects in production and utilization of glucose resulting in a failure to maintain appropriate blood sugar levels in the body. Diabetes in humans can be defined as a disorder corresponding to a fasting plasma glucose concentration greater than 125 mg/dL, or a plasma glucose concentration greater than 199 mg/dL two hours after ingestion of a 75 g oral glucose load. Two major forms of diabetes are type 1 diabetes (T1D) and type 2 diabetes (T2D). T1D is an autoimmune disorder resulting in destruction of beta-pancreatic cells and an absolute deficiency of insulin, the hormone that regulates glucose utilization. By contrast, T2D can occur with normal or even elevated levels of insulin from the inability of tissues to respond appropriately to insulin. Most T2D patients have impaired insulin sensitivity. Insulin secretion cannot compensate for the resistance of peripheral tissues to respond to insulin. Many T2D patients are obese. Type 1.5 diabetes (late autoimmune onset in adults) shows some characteristics of T1D and T2D.

Zinc is required for insulin biosynthesis and processing. Two zinc ions are complexed in a hexameric form of proinsulin, which is ultimately processed to insulin.

Gene SLC30A8 encodes an islet zinc transporter, ZnT8, predominantly expressed in the alpha and beta-pancreatic cells. It is expressed ten-fold higher in these cells than any other zinc transporters. Its expression is localized in secretory granule membranes where it transports zinc ions from the cytosol into vesicles. The protein has six transmembrane segments with both N and C-termini being intracellular. The fourth and fifth transmembrane segments, which are connected intracellularly by a histidine rich loop, form the ion channel for passage of zinc.

Genome-wide association studies have found single-nucleotide polymorphisms in the SLC30A8 gene with significant differences in genotype frequencies between cases of type 2 diabetes and controls (Sladek, R. et al., 2007, Nature, 445:881-885). Loci in the SLC30A8 gene were found that contain variants that confer T2D risk.

The major allele rs13266634 (C), encoding an arginine at position 325 (R325; W325R) was identified as a risk allele for T2D. (Sladek, 2007, supra; Rutter G. A. and Chimienti, F. 2104, Diabetologia 58:31-36). Sladek et al. (2007) supra report that the major allele at rs13266634 (C) is the ancestral allele and suggest that the ancestral allele was adapted to the environment of ancient human populations but today in a different environment, it increases disease risk. The minor allele rs13266634 (T) encodes an arginine to tryptophan substitution at position 325 (R325W; W325) in the SLC30A8 protein, encoding a protein with increased zinc transport activity. Individuals carrying the T allele (W325) have a reduced risk of T2D.

Various mutations in SLC30A8 have been reported. A common mutation R325W due to an rs13266634 C>T polymorphism, located in the C-terminal cytoplasmic tail, has been associated with increased levels of insulin and glucose and susceptibility to T2D (14% increased risk of T2D per R325 allele). Individuals with this mutation have reduced first phase insulin release and reduced proinsulin conversion. This mutation has been reported to reduce zinc transport activity but not change SLC30A8 expression significantly. Several rare mutations in which stop codons, frameshifts, splice site or initiator codon variants cause protein truncation, and presumably substantial loss of function of the truncated protein expressed, have a protective effect against T2D in heterozygous form in humans (Flannick et al., *Nat. Genet.* 46(4):357-363 (2014)). On average these mutations reduce the risk of T2D by 60%. Mice with a homozygous knockout of SLC30A8 have a heterogeneous phenotype depending on gender, genetic background, and nature of the knockout (e.g., all tissues or alpha or beta-pancreatic cell specific) varying from no overt effects to symptoms of T2D (Silva Xavier et al., *J. Diabetes Res.*, doi: 10.1155/2013/906590, Epub Apr. 11. 2013). A beta cell specific knockout has been reported to have increased proinsulin level, defects in insulin crystallization, and delayed and reduced first phase glucose-stimulated insulin secretion (Wijesekara et al., *Diabetologia* 53:1656-1668 (2010)) or decreased pancreatic zinc levels, increased insulin release and increased clearance of insulin by the liver (Tamaki et al., *J. Clin. Invest.* 123: 4513-4524 (2013)). However, the phenotypes of these SLC30A8 knockout mice have been inconsistent, making them unsuitable for a T2D disease model.

SUMMARY OF THE CLAIMED INVENTION

The invention provides a human induced pluripotent stem cell (iPSC) comprising in its genome two alleles of the SLC30A8 gene the same or different from each other. Optionally, the alleles are the same. Optionally, the alleles are different. Optionally, the alleles are R325. Optionally, the alleles are W325. Optionally, the alleles are R138*$^{stop}$. Optionally, one allele is R325 and one allele is W325. Optionally, one allele is R138 and one allele is R138*$^{stop}$. Optionally, the cell is a component of a clonal cell line. Such a cell can be generated by homologous recombination with a gene targeting construct bearing the mutation flanked by homology arms, wherein the recombination is enhanced by CRISPR/Cas9-mediated cleavage between segments of the genome corresponding to the homology arms. Optionally the gene targeting construct is an ssODN.

The invention further provides a cell culture comprising a population of cells defined as above in culture medium maintaining the pluripotent state. Optionally, the culture medium comprises MTESR medium and the cells are cultured on a surface coating matrix.

The invention further provides a method of modeling a beta-pancreatic cell, comprising culturing a cell as defined above under conditions promoting differentiation of the cell to a stem cell derived beta-pancreatic cell. Optionally, the cell is cultured under successive conditions as follows: RPMI medium supplemented by Activin A, CHIR99021, and B27; RPMI medium supplemented with activin A and B27; RPMI medium supplemented with FGF10, KAAD-cyclopamine, and B27; DMEM medium supplement with Noggin, KAAD-cyclopamine, retinoic acid, SB431542, and B27; CMRL medium supplemented with ALK5i, ILV, Noggin, and B27; and CMRL medium supplemented with excendin-4, nicotinamide, IBMX, FRKL, and B27. Optionally, the differentiation goes through the following stages: definitive endoderm, primitive gut tube, posterior foregut, pancreatic endoderm, and endocrine.

The invention further provides a cell produced by any of the above methods, characterized by one or more of the following properties: expression of nuclear protein NKX6-1, PDX-1, zinc transporter 8, and/or urocortin-3; insulin packaged into secretory granules; glucose-responsive insulin secretion; glucose-sensitive calcium flux; and/or glucose-sensitive C-peptide secretion. Optionally, the cell secretes insulin responsive to successive glucose challenges.

The invention further provides a cell culture comprising a population of cells of as defined in the previous paragraph and culture medium. Optionally, the culture medium comprises CMRL medium.

The invention further provides a method of screening a compound for activity for treating diabetes type 2 comprising: (a) contacting a stem cell derived beta-pancreatic cell as described herein with the compound; (b) determining glucose-induced insulin secretion relative to a control cell without the compound; and (c) selecting a compound wherein glucose-induced insulin secretion is changed relative to a control cell without the compound.

The invention further provides a method of producing a mouse model of diabetes type 2, comprising grafting a stem cell derived beta-pancreatic cell as described herein into an immunodeficient mouse, wherein the cell propagates forming beta-pancreatic tissue. Optionally the grafting comprises dissociating the cell from other cells in culture, treating the cell with a matrix promoting substance, and transplanting the treated cell into the mouse under the kidney capsule, wherein the cell propagates forming pancreatic tissue. Optionally, the mouse is a severe combined immunodeficient (SCID) mouse. Optionally, the mouse is a non-obese diabetic (NOD) mouse.

The invention further provides a method of screening a compound, comprising: (a) contacting a mouse produced by any of the above described methods with the compound; (b) determining a level of insulin or glucose relative to a control mouse not treated with the compound; and (c) selecting a compound wherein the level of insulin or glucose is changed relative to a control mouse not treated with the compound.

BRIEF DESCRIPTION OF THE DRAWINGS

FIG. 5 compares three protocols involving changes of media and additives for differentiation of hiPSC to stem cell derived beta-pancreatic cells.

DEFINITIONS

Figure 1:
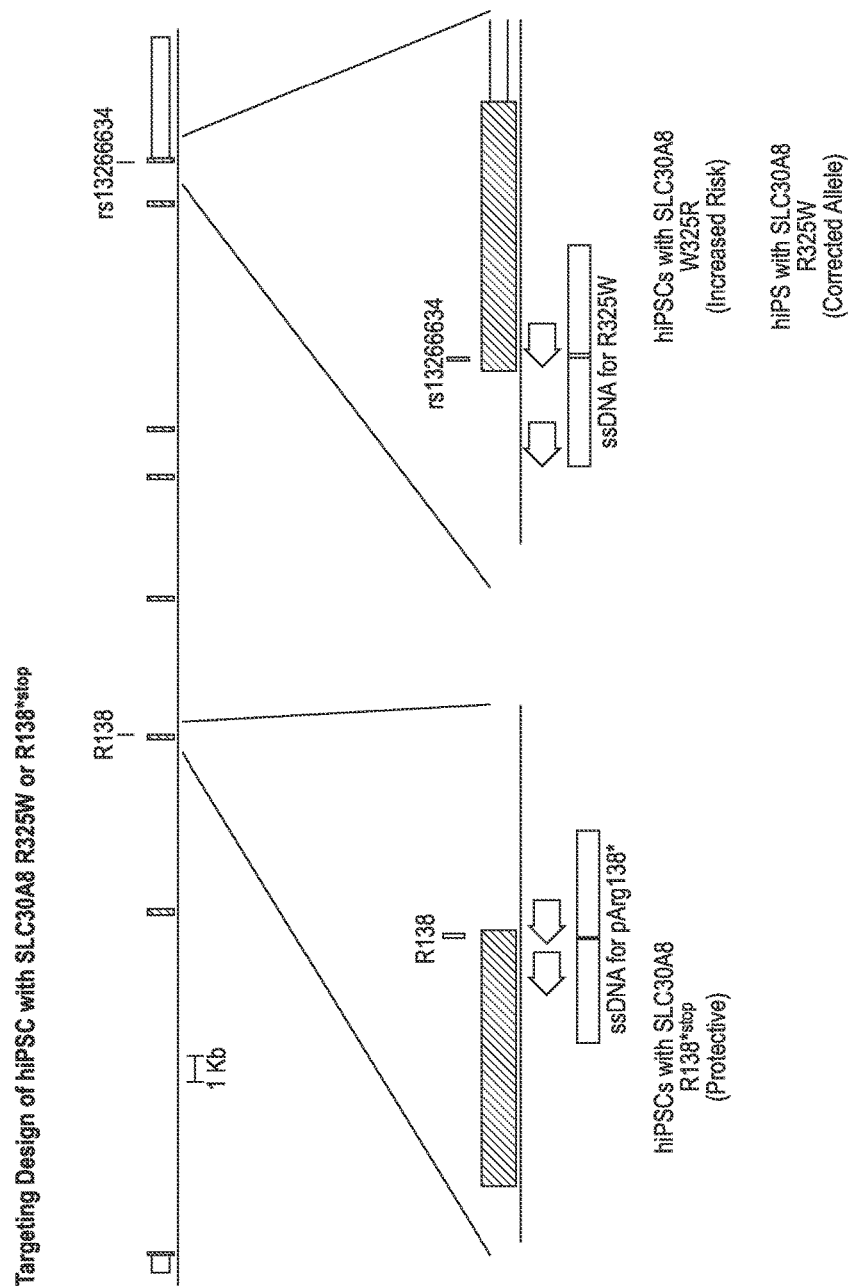
FIG. 1 shows an alignment of targeting constructs and the SLC30A8 gene locus.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

"Codon optimization" generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a Cas protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors.

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41 (% G+C), although other known Tm computations take into account nucleic acid structural characteristics.

"Hybridization condition" includes the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment. See, e.g., Sambrook et al., Molecular Cloning, A Laboratory Manual, $2^{nd}$ ed., pp. 1.90-1.91, 9.47-9.51, 11.47-11.57 (Cold Spring Harbor Laboratory Press, Cold Spring Harbor, N.Y., 1989), herein incorporated by reference in its entirety for all purposes.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, a gRNA in which 18 of 20 nucleotides are complementary to a target region, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs known in the art (Altschul et al. (1990) *J. Mol. Biol.* 215:403-410; Zhang and Madden (1997) *Genome Res.* 7:649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The methods and compositions provided herein employ a variety of different components. It is recognized throughout the description that some components can have active variants and fragments. Such components include, for example, Cas proteins, CRISPR RNAs, tracrRNAs, and guide RNAs. Biological activity for each of these components is described elsewhere herein.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" includes the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

Compositions or methods "comprising" or "including" one or more recited elements may include other elements not specifically recited. For example, a composition that "comprises" or "includes" a protein may contain the protein alone or in combination with other ingredients.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The singular forms of the articles "a," "an," and "the" include plural references unless the context clearly dictates otherwise. For example, the term "a Cas protein" or "at least one Cas protein" can include a plurality of Cas proteins, including mixtures thereof.

DETAILED DESCRIPTION

I. General

The invention provides human pluripotent stem cells, e.g., induced pluripotent stem cells (iPSs), comprising a mutation in the SLC30A8 gene that protects against or increases the risk of type 2 diabetes, beta-pancreatic cells derived from these human pluripotent stem cells, and animal models of T2D into which such cells have been grafted. An exemplary mutation in the SLC30A8 gene that increases the risk of T2D and is associated with susceptibility to T2D is R325 (also referred to herein as W325R). An exemplary mutation in the SLC30A8 gene that protects against and is associated with T2D resistance is W325 (also referred to herein as R325W and as corrected allele). An exemplary mutation in the SLC30A8 gene that protects against and is associated with T2D resistance is R138*$^{stop}$ (also referred to herein as p.Arg138X and as Arg138*$^{stop}$). The stem cells bear a mutated form of SLC30A8 conferring protection or susceptibility to T2D. The cells and animal models can be used for drug screening as well as to provide insights into the mechanism of T2D and potentially new therapeutic and diagnostic targets. Differentiated cells, e.g., pancreatic beta cells, can be derived from the human pluripotent stem cells. Animal models can comprise such differentiated cells.

An allele is a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

II. Induced Pluripotent Stem Cells

The term "pluripotent cell" or "pluripotent stem cell" includes an undifferentiated cell that possesses the ability to develop into more than one differentiated cell type. Such pluripotent cells can be, for example, a mammalian embryonic stem cell (ES cell) or a mammalian induced pluripotent stem cell (iPS cell). Examples of pluripotent cells include human iPS cells.

The term "embryonic stem cell" or "ES cell" means an embryo-derived totipotent or pluripotent stem cell, derived from the inner cell mass of a blastocyst, that can be maintained in an in vitro culture under suitable conditions. ES cells are capable of differentiating into cells of any of the three vertebrate germ layers, e.g., the endoderm, the ectoderm, or the mesoderm. ES cells are also characterized by their ability propagate indefinitely under suitable in vitro culture conditions. See, for example, Thomson et al. (Science (1998) Vol. 282(5391), pp. 1145-1147)

An induced pluripotent stem cell (iPSC or iPS cell) includes a pluripotent stem cell derivable from a differentiated adult cell, such as human foreskin cells. Human iPS cells can be generated by introducing specific sets of reprogramming factors into a non-pluripotent cell which can include, for example, Oct3/4, Sox family transcription factors (e.g., Sox1, Sox2, Sox3, Sox15), Myc family transcription factors (e.g., c-Myc, l-Myc, n-Myc), Krüppel-like family (KLF) transcription factors (e.g., KLF1, KLF2, KLF4, KLF5), and/or related transcription factors, such as NANOG, LIN28, and/or Glis1. For example, the reprogramming factors can be introduced into the cells using one or more plasmids, lentiviral vectors, or retroviral vectors. In some cases, the vectors integrate into the genome and can be removed after reprogramming is complete. In some cases, the vectors do not integrate (e.g., those based on a positive-strand, single-stranded RNA species derived from non-infectious (non-packaging) self-replicating Venezuelan equine encephalitis (VEE) virus, Simplicon RNA Reprogramming Kit, Millipore, SCR549 and SCR550). The Simplicon RNA replicon is a synthetic in vitro transcribed RNA expressing all four reprogramming factors (OKG-iG; Oct4, Klf4, Sox2, and Glis1) in a polycystronic transcript that is able to self-replicate for a limited number of cell divisions. Human induced pluripotent stem cells produced using the Simplicon kit are referred to as "integration-free" and "footprint-free." Human iPS cells can also be generated, for example, by the use of miRNAs, small molecules that mimic the actions of transcription factors, or lineage specifiers. Human iPS cells are characterized by their ability to differentiate into any cell of the three vertebrate germ layers, e.g., the endoderm, the ectoderm, or the mesoderm. Human iPS cells are also characterized by their ability propagate indefinitely under suitable in vitro culture conditions. See, for example, Takahashi and Yamanaka, *Cell* 126: 663-676 (2006)). Human iPS cells express alkaline phosphatase, SOX-2, OCT-4, Nanog and Tra-1-60 markers (e.g., at higher level than from the adult cells from which they were derived).

The terms "naïve" and "primed" identify different pluripotency states of human iPS cells. Characteristics of naïve and primed iPS cells are described in the art. See, for example, Nichols and Smith (Cell Stem Cell (2009) Vol. 4(6), pp. 487-492). Naïve human iPS cells exhibit a pluripotency state similar to that of ES cells of the inner cell mass of a pre-implantation embryo. Such naïve cells are not primed for lineage specification and commitment. Female naïve iPS cells are characterized by two active X chromosomes. In culture, self-renewal of naïve human iPS cells is dependent on leukemia inhibitory factor (LIF) and other inhibitors. Cultured naïve human iPS cells display a clonal morphology characterized by rounded dome-shaped colonies and a lack of apico-basal polarity. Cultured naïve cells can further display one or more pluripotency makers as described elsewhere herein. Under appropriate conditions, the doubling time of naïve human iPS cells in culture can be between 16 and 24 hours.

Primed human iPS cells express a pluripotency state similar to that of post-implantation epiblast cells. Such cells are primed for lineage specification and commitment. Female primed iPS cells are characterized by one active X chromosome and one inactive X chromosome. In culture, self-renewal of primed human iPS cells is dependent on fibroblast growth factor (FGF) and activin. Cultured primed human iPS cells display a clonal morphology characterized by an epithelial monolayer and display apico-basal polarity. Under appropriate conditions, the doubling time of primed human iPS cells in culture can be 24 hours or more.

III. SLC30A8

SLC30A8 maps to human 8q24.11 and has been assigned a genomic locus of 226,442 bases between bases 117962512 and 118188953 of chromosome 8 (Ref. Seq NM_001172811). The gene has been reported to have eight exons and seven introns. The wild type of human zinc transporter 8 (ZnT8) has been assigned Swiss-Prot accession number Q8IWU4. Two isoforms are known, Q8IWU4-1 and -2. The full-length protein has 369 amino acids including six transmembrane regions. The protein has four intracellular topological domains and two extracellular topological domains. Delineations between these domains are as designated in Swiss-Prot. Reference to SCL30A8 or ZnT8 includes the canonical (wild type) forms, as well as all allelic forms and isoforms. Any other forms of ZnT8 have amino acids numbered for maximal alignment with the wild type form, aligned amino acids being designated the same number. A codon 325 W to R substitution is associated with T2D susceptibility. An R325Q mutation is also known to exist but has not been associated with T2D. Flannick et al. (supra) describes 12 stop codon mutations, frameshifts, splice site or initiator codon variations cause protein truncation in SLC30A8 resulting in truncated proteins, which are protective against T2D when heterozygous. One of these is designated c.412 C>T, p.Arg138X meaning a C to T substitution at nucleotide 412 of the coding sequence results in an arginine residue at codon 138 being mutated to a stop codon (R138*$^{stop}$).

Polymorphisms in the SLC30A8 gene are associated with altered risk of T2D (Sladek, 2007, supra, Davidson, H. W. et al., 2014, Trends Endocrinol. Metabol. 25:415-424). The minor allele at rs168894362 (A) encodes a protein with glutamine at position 325 (referred to herein as R325Q).

A polymorphism or mutation in the SLC30A8 gene that increases risk of T2D includes a polymorphism or mutation in the SLC30A8 gene that confers susceptibility to T2D and a polymorphism or mutation in the SLC30A8 gene associated with susceptibility to T2D (e.g., those found in genome-wide association studies, Sladek, 2007, supra).

A polymorphism or mutation in the SLC30A8 gene that reduces risk of T2D includes a polymorphism or mutation in the SLC30A8 gene that confers protection against T2D, a polymorphism or mutation in the SLC30A8 gene that is protective against T2D, a polymorphism or mutation in the SLC30A8 gene that protects against T2D, a polymorphism or mutation in the SLC30A8 gene that confers resistance to T2D, and a polymorphism or mutation in the SLC30A8 gene that is associated with resistance to T2D (e.g., those found in genome-wide association studies, Sladek, 2007, supra).

IV. Gene Targeting and CRISPR/Cas Systems

Gene targeting is performed to introduce one or more mutations associated with susceptibility to T2D or protection against T2D into SLC30A8 in an iPSC. Exemplary targeting constructs include a contiguous segment of SLC30A8 including the site at which introduction of a mutation is sought. Targeting constructs can be vector-based targeting constructs or linear targeting constructs (e.g., single-stranded DNA targeting constructs). A linear targeting construct can be a single-stranded donor oligonucleotide (ssODN). The segment of SLC30A8 included in the targeting construct has the mutation sought to be introduced into the iPSC. The segment of SLC30A8 can be separated from unrelated vector sequences before being introduced into cells. After introduction into cells, the targeting construct undergoes homologous recombination with an endogenous SLC30A8 gene introducing the mutation into the genome of the cell. Preferably, the targeting construct is configured so that introduction of the desired mutation is the only change to the genome resulting from homologous recombination. The frequency of homologous recombination can be increased by effecting a double stranded cleavage in the genome within or nearby the segment of SLC30A8 undergoing homologous recombination with the targeting construct. Cleavage is preferably effected by co-transfection of the targeting construct with a system to deliver Cas and a guide RNA that directs cleavage by the Cas enzyme at the desired genomic location. In cells with a diploid genome, modification can occur at one or both alleles of the SLC30A8 gene. Modification at one allele resulting in a heterozygote more accurately models the situation in most human subjects having the mutations described.

The gene targeting construct and Cas gRNA delivery system are transfected into cells typically by electroporation. They can be introduced sequentially or concurrently. Cells bearing modifications can be initially selected by presence of markers either from a construct delivering Cas or gRNA or on the targeting construct. Additionally or alternatively, cells bearing modification can be identified by amplification of DNA and analysis with probes hybridizing across the site of the introduced mutation, or by sequencing across the site of the mutation among other methods.

Following transfection, selection and screening, a culture is established. The culture can be established from a single colony to generate a clonal cell line or from pooled colonies. The cells in a clonal cell line can be maintained in substantially identical form except for such mutation of differentiation as may spontaneously occur between cells.

The methods and compositions disclosed herein can utilize Clustered Regularly Interspersed Short Palindromic Repeats (CRISPR)/CRISPR-associated (Cas) systems or components of such systems to modify a genome within a cell. CRISPR/Cas systems include transcripts and other elements involved in the expression of, or directing the activity of, Cas genes. A CRISPR/Cas system can be a type I, a type II, or a type III system. The methods and compositions disclosed herein employ CRISPR/Cas systems by utilizing CRISPR complexes (comprising a guide RNA (gRNA) complexed with a Cas protein) for site-directed cleavage of nucleic acids.

CRISPR/Cas systems used in the methods disclosed herein can be non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together.

A. Cas RNA-Guided Endonucleases

Cas proteins generally comprise at least one RNA recognition or binding domain. Such domains can interact with guide RNAs (gRNAs, described in more detail below). Cas proteins can also comprise nuclease domains (e.g., DNase or RNase domains), DNA binding domains, helicase domains, protein-protein interaction domains, dimerization domains, and other domains. A nuclease domain possesses catalytic activity for nucleic acid cleavage. Cleavage includes the breakage of the covalent bonds of a nucleic acid molecule. Cleavage can produce blunt ends or staggered ends, and it can be single-stranded or double-stranded. A Cas protein can have full cleavage activity and create a double-strand break at a target genomic locus (e.g., a double-strand break with blunt ends), or it can be a nickase that creates a single-strand break at a target genomic locus.

Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

Cas proteins can be from a type II CRISPR/Cas system. For example, the Cas protein can be a Cas9 protein or be derived from a Cas9 protein. Cas9 proteins typically share four key motifs with a conserved architecture. Motifs 1, 2, and 4 are RuvC-like motifs, and motif 3 is an HNH motif. The Cas9 protein can be from, for example, *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina.* Additional examples of the Cas9 family members are described in WO 2014/131833, herein incorporated by reference in its entirety for all purposes. Cas9 protein from *S. pyogenes* or derived therefrom is a preferred enzyme. Cas9 protein from *S. pyogenes* is assigned SwissProt accession number Q99ZW2.

Cas proteins can be wild type proteins (i.e., those that occur in nature), modified Cas proteins (i.e., Cas protein variants), or fragments of wild type or modified Cas proteins. Cas proteins can also be active variants or fragments of wild type or modified Cas proteins. Active variants or fragments can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of the Cas protein.

Cas proteins can comprise at least two nuclease domains, such as DNase domains. For example, a Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, herein incorporated by reference in its entirety for all purposes.

One or both of the nuclease domains can be deleted or mutated so that they are no longer functional or have reduced nuclease activity. If one of the nuclease domains is deleted or mutated, the resulting Cas protein (e.g., Cas9) can be referred to as a nickase and can generate a single-strand break at a CRISPR RNA recognition sequence within a double-stranded DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null Cas protein). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839) or H840A (histidine to alanine at amino acid position 840) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes.

Cas proteins can also be fusion proteins. For example, a Cas protein can be fused to a cleavage domain, an epigenetic modification domain, a transcriptional activation domain, or a transcriptional repressor domain. See WO 2014/089290, herein incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

An example of a Cas fusion protein is a Cas protein fused to a heterologous polypeptide that provides for subcellular localization. Such heterologous polypeptides can include, for example, one or more nuclear localization signals (NLS) such as the SV40 NLS for targeting to the nucleus, a mitochondrial localization signal for targeting to the mitochondria, an ER retention signal, and the like. See, e.g., Lange et al. (2007) *J. Biol. Chem.* 282:5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence.

Cas proteins can also be linked to a cell-penetrating domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290, herein incorporated by reference in its entirety for all purposes. The cell-penetrating domain can be located at the N-terminus, the C-terminus, or anywhere within the Cas protein.

Cas proteins can also comprise a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g. eBFP, eBFP2, Azurite, mKalama1, GFPuv, Sapphire, T-sapphire), cyan fluorescent proteins (e.g. eCFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AUS, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. When a nucleic acid encoding the Cas protein is introduced into the cell, the Cas protein can be transiently, conditionally, or constitutively expressed in the cell.

Nucleic acids encoding Cas proteins can be stably integrated in the genome of a cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a vector comprising a DNA encoding a gRNA. Alternatively, it can be in a vector or plasmid that is separate from the vector comprising the DNA encoding the gRNA. Promoters that can be used in an expression construct include, for example, promoters active in a pluripotent rat, eukaryotic, mammalian, non-human mammalian, human, rodent, mouse, or hamster cell. Examples of other promoters are described elsewhere herein. Such promoters can be, for example, conditional promoters, inducible promoters, constitutive promoters, or tissue-specific promoters.

B. Guide RNAs (gRNAs)

A "guide RNA" or "gRNA" includes an RNA molecule that binds to a Cas protein and targets the Cas protein to a specific location within a target DNA. Guide RNAs can comprise two segments: a "DNA-targeting segment" and a "protein-binding segment." "Segment" includes a segment, section, or region of a molecule, such as a contiguous stretch of nucleotides in an RNA. Some gRNAs comprise two separate RNA molecules: an "activator-RNA" and a "targeter-RNA." Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. The terms "guide RNA" and "gRNA" include both double-molecule gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA" or "scaffold") molecule. A crRNA comprises both the DNA-targeting segment (single-stranded) of the gRNA and a stretch of nucleotides that forms one half of the dsRNA duplex of the protein-binding segment of the gRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA.

The crRNA and the corresponding tracrRNA hybridize to form a gRNA. The crRNA additionally provides the single-stranded DNA-targeting segment that hybridizes to a CRISPR RNA recognition sequence. If used for modification within a cell, the exact sequence of a given crRNA or tracrRNA molecule can be designed to be specific to the species in which the RNA molecules will be used. See, for e.g., Mali et al. (2013) *Science* 339:823-826; Jinek et al. (2012) *Science* 337:816-821; Hwang et al. (2013) *Nat. Biotechnol.* 31:227-229; Jiang et al. (2013) *Nat. Biotechnol.*

31:233-239; and Cong et al. (2013) *Science* 339:819-823, each of which is herein incorporated by reference in its entirety for all purposes.

The DNA-targeting segment (crRNA) of a given gRNA comprises a nucleotide sequence that is complementary to a sequence in a target DNA. The DNA-targeting segment of a gRNA interacts with a target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the Cas9 system and organism but often contain a targeting segment of between 21 to 72 nucleotides length, flanked by two direct repeats (DR) of a length of between 21 to 46 nucleotides (see, e.g., WO2014/131833, herein incorporated by reference in its entirety for all purposes). In the case of *S. pyogenes*, the DRs are 36 nucleotides long and the targeting segment is 30 nucleotides long. The 3' located DR is complementary to and hybridizes with the corresponding tracrRNA, which in turn binds to the Cas9 protein.

The DNA-targeting segment can have a length of from about 12 nucleotides to about 100 nucleotides. For example, the DNA-targeting segment can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, or from about 12 nt to about 19 nt. Alternatively, the DNA-targeting segment can have a length of from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 19 nt to about 70 nt, from about 19 nt to about 80 nt, from about 19 nt to about 90 nt, from about 19 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

The nucleotide sequence of the DNA-targeting segment that is complementary to a nucleotide sequence (CRISPR RNA recognition sequence) of the target DNA can have a length at least about 12 nt. For example, the DNA-targeting sequence (i.e., the sequence within the DNA-targeting segment that is complementary to a CRISPR RNA recognition sequence within the target DNA) can have a length at least about 12 nt, at least about 15 nt, at least about 18 nt, at least about 19 nt, at least about 20 nt, at least about 25 nt, at least about 30 nt, at least about 35 nt, or at least about 40 nt. Alternatively, the DNA-targeting sequence can have a length of from about 12 nucleotides (nt) to about 80 nt, from about 12 nt to about 50 nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, from about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some cases, the DNA-targeting sequence can have a length of at least about 20 nt.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise or consist of all or a portion of a wild-type tracrRNA sequence (e.g., about or more than about 20, 26, 32, 45, 48, 54, 63, 67, 85, or more nucleotides of a wild-type tracrRNA sequence). Examples of wild-type tracrRNA sequences from *S. pyogenes* include 171-nucleotide, 89-nucleotide, 75-nucleotide, and 65-nucleotide versions. See, e.g., Deltcheva et al. (2011) *Nature* 471:602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild-type tracrRNA is included in the sgRNA. See U.S. Pat. No. 8,697,359, herein incorporated by reference in its entirety for all purposes.

The percent complementarity between the DNA-targeting sequence and the CRISPR RNA recognition sequence within the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting sequence and the CRISPR RNA recognition sequence within the target DNA can be at least 60% over about 20 contiguous nucleotides. As an example, the percent complementarity between the DNA-targeting sequence and the CRISPR RNA recognition sequence within the target DNA is 100% over the 14 contiguous nucleotides at the 5' end of the CRISPR RNA recognition sequence within the complementary strand of the target DNA and as low as 0% over the remainder. In such a case, the DNA-targeting sequence can be considered to be 14 nucleotides in length. As another example, the percent complementarity between the DNA-targeting sequence and the CRISPR RNA recognition sequence within the target DNA is 100% over the seven contiguous nucleotides at the 5' end of the CRISPR RNA recognition sequence within the complementary strand of the target DNA and as low as 0% over the remainder. In such a case, the DNA-targeting sequence can be considered to be 7 nucleotides in length.

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof.

Exemplary chimeric gRNAs comprising a nucleic acid sequence encoding a crRNA and a tracrRNA include (SEQ ID NO: 1)
5'-GUUUUAGAGCUAGAAAUAGCAAGUUAAAAUAAGGCUAGUCCGUUAUC AACUUGAAAAAGUGGCACCGAGUCGGUGCUUUU-3';
or (SEQ ID NO: 2)
5'-GUUUUAGAGCUAGAAAUAGCAAGUUAAAAUAAGGCUAGUCCG-3'.

Exemplary crRNAs include (SEQ ID NO: 3)
5'-GUUUUAGAGCUAGAAAUAGCAAGUUAAAAU-3';

(SEQ ID NO: 4)
5'-GUUUUAGAGCUAGAAAUAGCAAGUUAAAAUAAG;
or (SEQ ID NO: 5)
5'-GAGUCCGAGCAGAAGAAGAAGUUUUA-3'.

Exemplary tracrRNAs include (SEQ ID NO: 6)
5'-AAGGCUAGUCCG-3'
or (SEQ ID NO: 7)
5'-AAGGCUAGUCCGUUAUCAACUUGAAAAAGUGGCACCGAGUCGGUGCU

UUU-3'.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a DNA encoding a gRNA is introduced into a cell, the gRNA can be transiently, conditionally, or constitutively expressed in the cell. DNAs encoding gRNAs can be stably integrated in the genome of the cell and operably linked to a promoter active in the cell. Alternatively, DNAs encoding gRNAs can be operably linked to a promoter in an expression construct. For example, the DNA encoding the gRNA can be in a vector comprising a nucleic acid encoding a Cas protein. Alternatively, it can be in a vector or a plasmid that is separate from the vector comprising the nucleic acid encoding the Cas protein. Such promoters can be active, for example, in a pluripotent rat, eukaryotic, mammalian, non-human mammalian, human, rodent, mouse, or hamster cell. Such promoters can be, for example, conditional promoters, inducible promoters, constitutive promoters, or tissue-specific promoters. In some instances, the promoter is an RNA polymerase III promoter, such as a human U6 promoter, a rat U6 polymerase III promoter, or a mouse U6 polymerase III promoter. Examples of other promoters are described elsewhere herein.

Alternatively, gRNAs can be prepared by various other methods. For example, gRNAs can be prepared by in vitro transcription using, for example, T7 RNA polymerase (see, e.g., WO 2014/089290 and WO 2014/065596), each of which is herein incorporated by reference in its entirety for all purposes. Guide RNAs can also be a synthetically produced molecule prepared by chemical synthesis.

C. CRISPR RNA Recognition Sequences

The term "CRISPR RNA recognition sequence" includes nucleic acid sequences present in a target DNA to which a DNA-targeting segment of a gRNA will bind, provided sufficient conditions for binding exist. For example, CRISPR RNA recognition sequences include sequences to which a guide RNA is designed to have complementarity, where hybridization between a CRISPR RNA recognition sequence and a DNA targeting sequence promotes the formation of a CRISPR complex. Full complementarity is not necessarily required, provided there is sufficient complementarity to cause hybridization and promote formation of a CRISPR complex. CRISPR RNA recognition sequences also include cleavage sites for Cas proteins, described in more detail below. A CRISPR RNA recognition sequence can comprise any polynucleotide, which can be located, for example, in the nucleus or cytoplasm of a cell or within an organelle of a cell, such as a mitochondrion or chloroplast.

The CRISPR RNA recognition sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001) herein incorporated by reference in its entirety for all purposes). The strand of the target DNA that is complementary to and hybridizes with the Cas protein or gRNA can be called the "complementary strand," and the strand of the target DNA that is complementary to the "complementary strand" (and is therefore not complementary to the Cas protein or gRNA) can be called "noncomplementary strand" or "template strand."

The Cas protein can cleave the nucleic acid at a site within or outside of the nucleic acid sequence present in the target DNA to which the DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to a CRISPR RNA recognition sequence and complexed with a Cas protein) can result in cleavage of one or both strands in or near (e.g., within 1, 2, 3, 4, 5, 6, 7, 8, 9, 10, 20, 50, or more base pairs from) the nucleic acid sequence present in a target DNA to which a DNA-targeting segment of a gRNA will bind. If the cleavage site is outside of the nucleic acid sequence to which the DNA-targeting segment of the gRNA will bind, the cleavage site is still considered to be within the "CRISPR RNA recognition sequence." The cleavage site can be on only one strand or on both strands of a nucleic acid. Cleavage sites can be at the same position on both strands of the nucleic acid (producing blunt ends) or can be at different sites on each strand (producing staggered ends (i.e., overhangs)). Staggered ends can be produced, for example, by using two Cas proteins, each of which produces a single-strand break at a different cleavage site on each strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the CRISPR RNA recognition sequence of the nickase on the first strand is separated from the CRISPR RNA recognition sequence of the nickase on the second strand by at least 2, 3, 4, 5, 6, 7, 8, 9, 10, 15, 20, 25, 30, 40, 50, 75, 100, 250, 500, or 1,000 base pairs.

Site-specific cleavage of target DNA by Cas9 can occur at locations determined by both (i) base-pairing complementarity between the gRNA and the target DNA and (ii) a short motif, called the protospacer adjacent motif (PAM), in the target DNA. The PAM can flank the CRISPR RNA recognition sequence. Optionally, the CRISPR RNA recognition sequence can be flanked on the 3' end by the PAM. For example, the cleavage site of Cas9 can be about 1 to about 10 or about 2 to about 5 base pairs (e.g., 3 base pairs) upstream or downstream of the PAM sequence. In some cases (e.g., when Cas9 from *S. pyogenes* or a closely related Cas9 is used), the PAM sequence of the non-complementary strand can be 5'-$N_1$GG-3', where $N_1$ is any DNA nucleotide and is immediately 3' of the CRISPR RNA recognition sequence of the non-complementary strand of the target DNA. As such, the PAM sequence of the complementary strand would be 5'-$CCN_2$-3', where $N_2$ is any DNA nucleotide and is immediately 5' of the CRISPR RNA recognition sequence of the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T, or $N_1$=T, and $N_2$=A).

Examples of CRISPR RNA recognition sequences include a DNA sequence complementary to the DNA-targeting segment of a gRNA, or such a DNA sequence in addition to a PAM sequence. For example, the target motif can be a 20-nucleotide DNA sequence immediately preceding an NGG motif recognized by a Cas protein, such as $GN_{19}NGG$ (SEQ ID NO: 8) or $N_{20}NGG$ (SEQ ID NO: 9) (see, e.g., WO 2014/165825, herein incorporated by reference in its entirety for all purposes). The guanine at the 5' end can facilitate transcription by RNA polymerase in cells. Other examples of CRISPR RNA recognition sequences can include two guanine nucleotides at the 5' end (e.g., $GGN_{20}NGG$; SEQ ID NO: 10) to facilitate efficient transcription by T7 polymerase in vitro. See, e.g., WO 2014/065596, herein incorporated by reference in its entirety for all purposes. Other CRISPR RNA recognition sequences can have between 4-22 nucleotides in length of SEQ ID NOS: 8-10, including the 5' G or GG and the 3' GG or NGG. Yet other CRISPR RNA recognition sequences can have between 14 and 20 nucleotides in length of SEQ ID NOS: 8-10. Specific examples of CRISPR RNA recognition sequences include DNA sequences comprising any one of SEQ ID NOs: 11 and 13. The CRISPR RNA recognition sequence can be any nucleic acid sequence endogenous or exogenous to a cell. The CRISPR RNA recognition sequence can be a sequence coding a gene product (e.g., a protein) or a non-coding sequence (e.g., a regulatory sequence) or can include both.

V. Culturing Cells (1) Homeostasis

Before introduction of targeting constructs into hiPSCs, it is desirable to maintain the cells in their pluripotent state. Cells can also be maintained in their pluripotent state after introduction of targeting constructs to provide cells an opportunity to recover from the transfection process and propagate before performing subsequent procedures.

hiPSCs can be cultured maintaining a pluripotent state in MTESR media from Stemcell Technologies Inc. and on a surface-coating matrix-promoting substance, which can be vitronectin or MATRIGEL matrix, among others. MTESR medium is a complete serum-free defined formulation containing recombinant human basic FGF, and recombinant human TGFbeta. Media is preferably changed daily. hiPSCs are characterized by homogeneous phenotype and normal human karyotype (46 chromosomes) and high expression of genes associated with undifferentiated pluripotent stem cells (e.g., Oct4, SSEA-3, SSEA-4, TRA-1-60, TRA-1-81, Nanog SOX3 and ECAD). The cells can undergo directed differentiation to mature cell types of any of mesoderm, endoderm and ectoderm. The cells grow as compact, multicellular colonies characterized by distinct borders. Individual cells are tightly packed and show a high nuclear to cytoplasm ratio and have prominent nucleoli. Spontaneous differentiation is characterized by loss of colony border integrity, regions of irregular cell morphology within a colony and/or emergence of other cell types.

Figure 4:
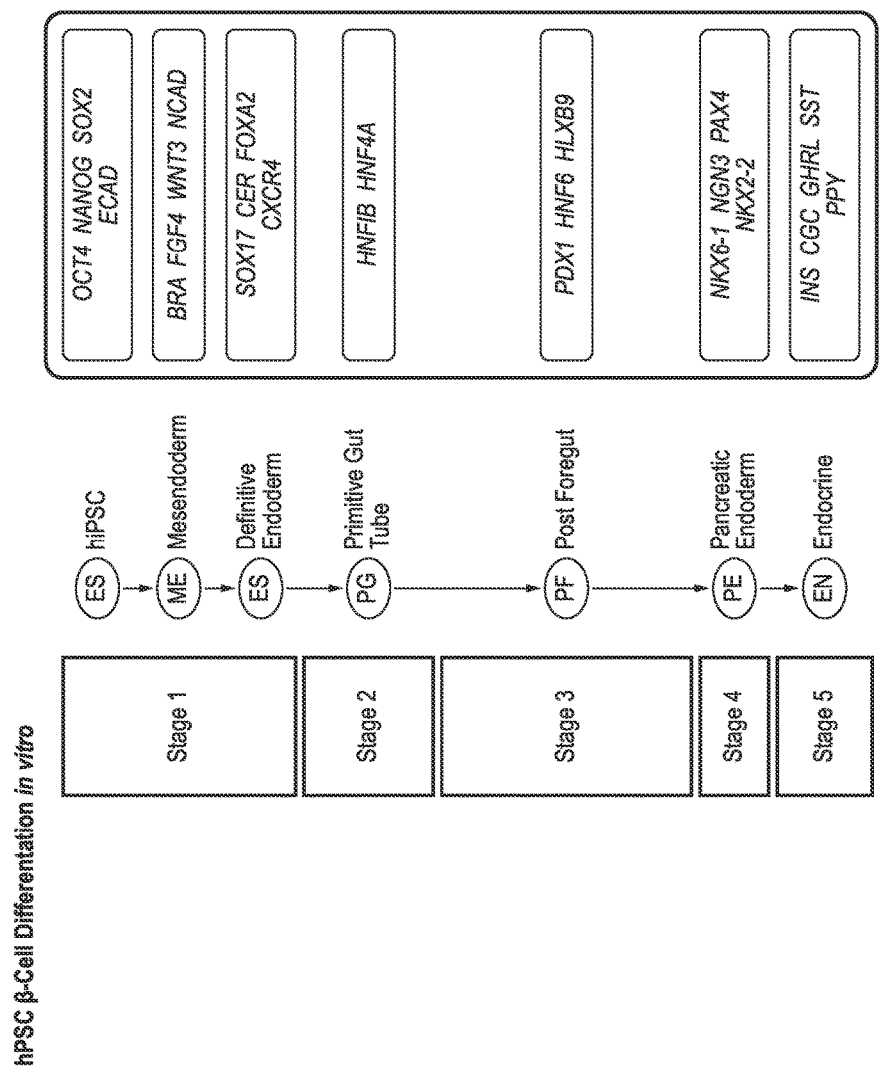
FIG. 4 shows changes in differentiation markers between hiPSCs and stem cell derived endocrine cells.

(2) Differentiation hiPSC can be induced to differentiate into cells resembling adult model beta-pancreatic cells. Such cells are referred to as stem cell derived beta-pancreatic cells. The differentiation procedures can comprise progression through several intermediate stages characterized by distinct markers. Differentiation through these stages to stem cell derived beta-pancreatic cells is driven by changes of media and supplements. The stages in the differentiation pathway from iPSC can include any and usually all of the following: definitive endoderm, primitive gut tube, posterior foregut, pancreatic endoderm, and endocrine. FIG. 4 shows an exemplary progression of differentiation markers for in vitro differentiation of hiPSC to endocrine cells. Differentiation markers for these stages include BRA, FGF4, WNT3 and NCAD for mesendoderm; Sox17, FoxA2, CXCR4 for definitive endoderm; HNF1B, HNF4A for primitive gut tube; PDX1, HNF6 and HLXB9 for post foregut; NKX6-1, NGN3, PAX5 and NKx2-2 for pancreatic endoderm; and INS, CGF, GHRL, SST and PPY for endocrine. Stages may have any or all (e.g., at least 1, 2, 3, 4, 5 or all) of the properties indicated.

An exemplary succession of media is Roswell Park Memorial Institute medium (RPMI), e.g., RPMI 1640 (from Sigma, Life Technologies) until the primitive gut tube cell type is reached; Dulbecco modified Eagle's medium (DMEM) (e.g., Sigma) until posterior foregut is reached; and Connaught Medical Research Laboratories media (CMRL) (e.g., Sigma) thereafter. Different supplements have been described by different authors (D'Amour et al., *Nature Biotech.* 24:1392-1401 (2006); Hua et al., *J. Clin. Invest.* 123:3146-3153 (2013); and Shahjalal et al., *J. Molec. Cell. Biol.* 6(5):394-408 (2014) (also referred to herein as Kume) as summarized in FIG. 5. The common features of the methods include use of RPMI media and activin A at the definitive endoderm stage; use of RPMI media, FGF10 and KAADS cylopamine at the primitive gut stage; use of DMEM media, FGF10, KAAD-cyclopamine, retinoic acid and B27 at the posterior foregut stage; and use of CMRL media, and B27 at the pancreatic endoderm stage and endocrine stage.

The present hiPS cells can be differentiated following any of the procedures by D'Amour, Hua or Shahjalal (i.e., Kume), or permutations or variations thereof. The present hiPS cells can also be differentiated following any of the procedures (or permutations or variations thereof) by Pagliuca & Melton, *Development,* 140:2472-2483 (2013) or Pagliuca et al., *Cell* 159:428-439 (2014). For example, the methods can be practiced using the core selections of media and additives common to all or some of the methods, optionally supplemented by one or more the other additives used in any of the methods. Concentrations of additives can be as indicated in FIG. 5 but can also be varied by +/−up to 10, 20, 50, 100 or 200%.

Differentiation to endocrine cells can take from e.g., about 10 to 40 days or 13-35, or 13-23 days depending on the media and supplements selected. Stem cell derived beta-pancreatic cells express markers found in mature beta cells, such as any or all of cytoplasmic C-peptide, nuclear protein NKX6-1, PDX-1, zinc transporter 8 and/or urocortin-3. The cells can express any combination of the markers. The cells can also have any or all of the following properties (e.g., at least 1, 2, 3, 4, 5, 6 or 7): cells are glucose responsive, flux calcium in response to glucose, package insulin into secretory granules, secrete insulin in response to glucose preferably in comparable amounts to adult beta cells, secrete insulin in response to multiple sequential glucose challenges, secrete C-peptide in response to glucose; possess endogenous pools of insulin or proinsulin. The cells can have any combination of the properties. By transcriptome analysis, stem cell derived beta-pancreatic cells cluster most closely with adult human pancreatic beta cells than with the starting hiPSCs or other common adult cells (pancreatic alpha cells, liver, brain, heart, lungs, muscle, and skin).

VI. Generation of Animal Models

Stem-cell derived beta-pancreatic cells are grafted into a recipient animal. Preferably the animal is immunodeficient to suppress rejection of the grafted stem cells, although alternatively or additionally immune responses can be suppressed by immunosuppressive drugs. The animal is preferably a mammal, such as a rodent, for example, a mouse, rat or rabbit. Alternatively, the animal can be a fish, such as a zebrafish, or an insect. Well-known examples of immunodeficient mice include nude mice, SCID mice, NOD mice, RAG1-null or RAG2-null mice, NOD-SCID mice, IL-2Rgamma-null mice, B2M-null mice, H2-Abl-null mice (see Belizario, Open Immunol. J. 2:79-85 (2009)). Animal models may or may not have other characteristics conferring susceptibility or resistance to T2D. For example, NOD mice have a predisposition to T2D irrespective of the transplanted cells. Transgenic or other animal models of type 2 diabetes include HIP rats, db/db mice, Zucker diabetic fatty rats, ob/ob mice, high calorie-fed Psammomys obesus (sand rats), Goto-Katazaki rats (GK rats), and RIPHAT transgenic mice. Rodent models of type 1 diabetes include spontaneous autoimmune models including NOD mice, BB rats, and LEW.1AR1/-iddm rats and genetically induced models including AKITA mice. Rodent models of type 2 diabetes include obese models (monogenic) including Lepob/ob mice, Leprdb/db mice, and ZDF rats; obese models (polygenic) including KK mice, OLETF rat, NZO mice, TallyHo/jng mice, and NoncNZO10/Ltj mice; induced obesity models including high fat feeding (mice or rats), Desert gerbil, and Nile grass rat; non-obese models including GK rat; and genetically induced models of beta cell dysfunction including hiAPP mice and AKITA mice. (King, A. J. F. 2012, Brit. Jour. Pharmacol. 166:877-894). Cells are preferably dissociated before grafting into a recipient animal and combined with a matrix promoting compound, such as vitronectin or MATRIGEL matrix. Cell can be inserted below the kidney in the renal subcapsule among other locations (see, e.g., Li et al., Protocol Exchange (2011) doi:10.1038/pro-tex.2011.221; Hua et al., J. Clin. Invest. 123:3146-3153 (2013); and Szot et al., J. Vis. Exp. (2007) doi: 10.3791/404). After grafting, animals are allowed to develop for a period during which the grafted cells can undergo further differentiation to more closely resemble adult pancreatic beta cells. The period of development can be at least a week, a month or at least three months. In some mice, grafted cells begin to function about two weeks after transplantation. In some mice with irradiated islets before grafting, stem cell derived beta-pancreatic cells can fully replace the insulin response of the irradiated cells. In some mice having a diabetes phenotype before grafting, the stem cell derived beta-pancreatic cells can reverse the diabetes phenotype.

Comparison between animals grafted with SLC30A8 mutations conferring protection and susceptibility to T2D provides further information in identifying the mechanism by which SLC30A8 contributes to insulin processing and diabetes. Molecules expressed at higher levels or having higher activity in animals with a susceptibility mutation than a protective mechanism are identified as potential targets for treatment or diagnosis of T2D.

VII. Drug Screening Methods

Stem cell-derived beta-pancreatic cells and animals into which such cells have been grafted can be used for screening compounds for activity potentially useful in inhibiting or reducing T2D or potentially harmful in promoting or exacerbating T2D. Compounds having activity inhibiting or reducing T2D are potentially useful as therapeutics or prophylactics against T2D. Compounds having activity promoting or exacerbating T2D are identified as toxic and should be avoided as therapeutics or in other circumstances in which they may come into contact with humans (e.g., in foods, agriculture, construction, or water supply).

Examples of compounds that can be screened include antibodies, antigen-binding proteins, polypeptides, beta-turn mimetic s, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described WO 95/12608, WO 93/06121, WO 94/08051, WO 95/35503 and Scripps, WO 95/30642. Peptide libraries can also be generated by phage display methods. See, e.g., U.S. Pat. No. 5,432,018.

Cellular assays generally involve contacting a stem cell derived beta-pancreatic cell (or more typically a culture of such cells) with a compound and determining whether a property of the cells changes. The change can be assessed from levels of the property before and after contacting the cell with the compound or by performing a control experiment performed on the same cell or population of cells without the compound. The property measured is often a level of insulin secreted by the cell or proinsulin within a cell. The screening may also include treating the cell with an agent inducing secretion of insulin, such as glucose, arginine or a secretagogue, and measuring insulin secreted in response. Optionally, the insulin secretion response can be measured in response to successive challenges of the inducing agent.

Analogous experiments can be performed on an animal into which stem cell derived beta-pancreatic cells have been grafted except that signs and symptoms more closely resembling those of T2D in a human can be assessed for change in response to administering a compound. Suitable signs or symptoms that can be monitored include elevated blood glucose levels (e.g., fasting blood glucose levels or blood glucose levels following an oral glucose challenge), and insulin levels. Glucose tolerance refers to a state of proper functioning of the homeostatic mechanisms by which insulin is secreted in response to an elevation in serum glucose concentrations.

A normal level of glucose in human is in the range of from about 65 mg/dL to about 140 mg/dL. Impairment in this system results in transient hyperglycemia as the organism is unable to maintain normoglycemia following a glucose load (for example, a carbohydrate containing meal) because of insufficient secretion of insulin from the islet beta-cells or because of insensitivity of target tissues to circulating insulin. Impaired glucose tolerance in humans can be defined as a plasma glucose concentration greater than or equal to 140 mg/dl (7.8 mmol/1) two hours after ingestion of a 75 g oral glucose load. Impaired insulin sensitivity can be determined by IV glucose tolerance test (FSIVGTT), insulin tolerance test (ITT), insulin sensitivity test (1ST), and continuous infusion of glucose with model assessment (CIGMA), or the glucose clamp. See, e.g., Krentz, Insulin Resistance (Wiley-Blackwell, 2002); de Paula Martins et al., *Eur. J. Obst. Gynecol. Reprod. Biol.* 133(2):203-207 (2007). Normal ranges of blood sugar in mice are 60-130 mg/ml, similar to those in humans.

All of these tests for detection of glucose, insulin and other metabolites for humans can be performed with minor modifications (e.g., use 75 mg not 75 g of glucose for oral challenge) in mice (Pacini et al., *Journal of Diabetes Research*, doi: 10.1155/2013/986906 (2013)). The oral glucose challenge test mimics the normal route of assuming carbohydrates. The ingested glucose (usually instilled into the stomach) is absorbed in the intestinal tract and enters the splanchnic circulation and then into the systemic circulation. The increased blood glucose concentration stimulates the pancreatic beta cell to release insulin, which stimulates glucose uptake by peripheral tissues. The passage of the nutrients through the early part of the intestine stimulates the release of the gut hormones (e.g., glucose-dependent insulinotropic polypeptide, GIP, and glucagon-like peptide-1, GLP-1), which in turn augment the beta cell sensitivity to glucose, increasing the production of insulin.

In an exemplary procedure, in a 30 min period after anesthesia, a gavage tube (outer diameter 1.2 mm) is placed in the stomach to be used to administer glucose (dose 75 mg/mouse) in few seconds (standardized volume of 0.5 mL, approximate energy content 0.171 kcal). Blood samples are collected from the retrobulbar, intraorbital, capillary plexus into heparinized tubes before and either 5, 10, and 20 min or 15, 30, 60, and 90 min after oral gavage.

Changes in a level of glucose, insulin or other analyte can be determined by comparison with an appropriate control, such as blood glucose levels in control animals that have not received the compound, or control animals which have received stem cell derived beta-pancreatic cells not bearing the mutations of the SLC30A8 gene disclosed herein. Existing drugs for T2D can be used as positive controls (e.g., sulfonylureas biguanides, meglitinides, thiazolidinediones, DPP-4 inhibitors, SGLT2 Inhibitors, alpha-glucosidase inhibitors, and bile acid sequestrants).

EXAMPLES

Example 1

Introduction of Targeted Mutations in the SLC30A8 Gene into hiPSCs

This example describes the introduction of targeted mutations in the SLC30A8 gene into hiPSCs.

hiPSC were electroporated with a vector encoding Cas9 and guide RNA and a puromycin resistance gene and a linear target construct comprising an R138*$^{stop}$ or R325W mutation flanked by homology arms. The starting BJ human foreskin fibroblasts carry the major allele at rs13266634 (cytosine (C)) and thus encode an arginine at position 325 (as determined by Next Generation Sequencing (NGS) at Regeneron). One linear target construct was designed to introduce the minor allele rs13266634 (thymine (T)) and thus encode an arginine to tryptophan substitution at position 325 (R325W) in the SLC30A8 protein. The other linear target construct was designed to introduce a stop codon in the SLC30A8 DNA at the position encoding arginine 138, resulting in the production of a truncated SLC30A8 protein. The Cas9 expression vector comprises: (1) a CAGG promoter operably linked to a Cas9 gene, (2) a human U6 promoter operably linked to a sgRNA, and (3) an EF-1 alpha promoter that drives expression of GFP and a puromycin gene in a bicistronic manner using T2A (Thoseaasigna virus 2A peptide; incorporated by reference herein (Kim et al, PLoS, 2011, DOI:10.1371).

The sequences of the targeting constructs and DNAs encoding gRNAs are shown below. The guide RNA was complementary to genomic DNA proximate to the R138*$^{stop}$ or R325W mutation. The guide RNA and targeting constructs used in this example were as follows.

```
                                        (SEQ ID NO: 11)
    sg138*stop: GCTCTATGAACCGTACCTGCT ssDNA for R138*stop:
                                        (SEQ ID NO: 12)
TTGGTTTGACTTTGCAGCACCAGCCTGCTGTTATTGCTCACTCTATGAAC

CGTACCTGCTCAGTGCCATCCAAATGTCAGCCGCTTAGAGGGAGGCTTCG

ATGACAACCACAGGGAGAAGA sgR325W:
                                        (SEQ ID NO: 13)
GAACCACTTGGCTGTCCCGGC ssDNA for (SEQ ID NO: 14)
R325W: GCATCGTAAAGCTTTTGCTAAGGGCTTTAGCAATTTCTCTCCG

AACCACTTGGCTGTCCCAGCTGGCTGCTGTTGATAAAGAAGCACAGGGAG

ATTAGCACTGATTGCACACGCATGGGCG
```

Figure 2:
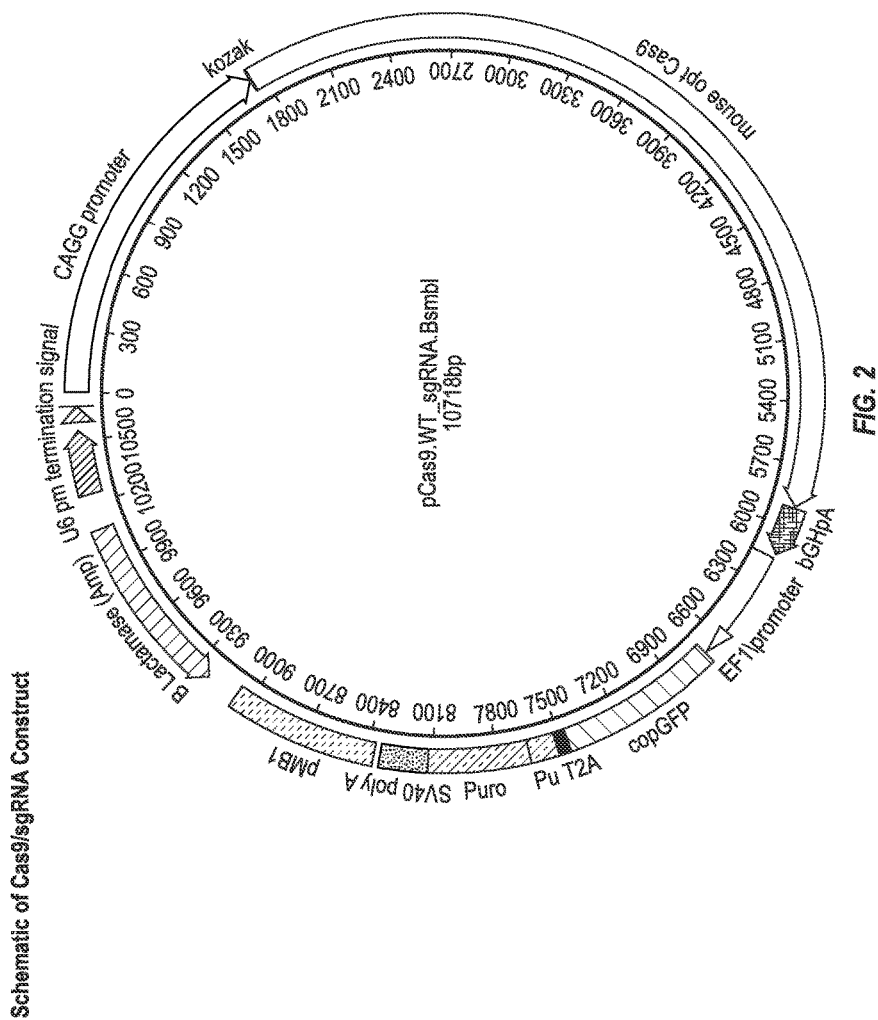
FIG. 2 shows a vector for expressing Cas9 and gRNA, and also a work flow for screening cells transformed with this vector and a targeting construct.
Figure 3:
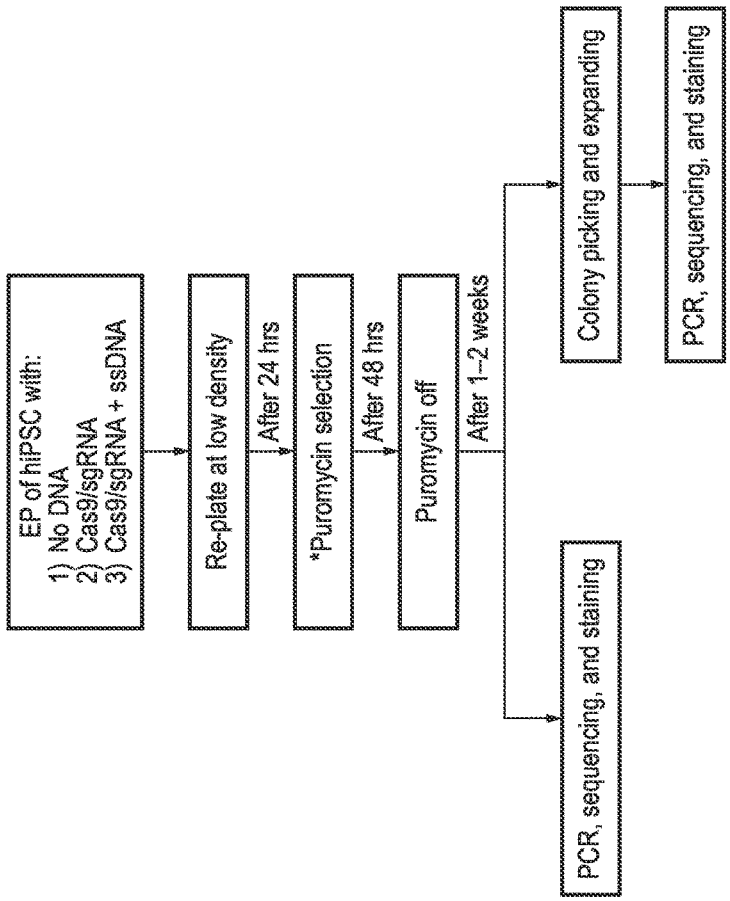
FIG. 3 shows a work flow for analysis of transfectants by PCR or sequencing.

An alignment of the targeting constructs with the genomic locus being targeted is shown in FIG. 1. The vector encoding Cas9 and the guide RNA is shown in FIG. 2. FIG. 2 also shows the controls and time line for plating and selection. Controls omitted all DNA or omitted targeting constructs. Electroporated cells were replated at low density and after 24 hr subjected to puromycin selection for 48 hours. After a further 1-2 weeks growth without purifying, colonies were picked and analyzed for presence of an R138*$^{stop}$ or R325W mutation by PCR and sequencing. FIG. 3 shows a work flow for selection and analysis.

Transient GFP expression was observed in cells tested 24 hours after electroporation with (1) pCas9+SLC30A8 R138* ssODN; or (2) pCas9+SLC30A8 R325W ssODN, indicating expression of gene products from the pCas9 vector. The no DNA control showed no colonies expressing GFP.

In some cases, PCR products were run on the MiSeq to assess the data and screen for correctly recombined clones as well as for non-homologous end joining (NHEJ) events.

hiPSCs carrying the following SLC30A8 alleles were obtained:
Homozygous R325/R325
Homozygous W325/W325
Homozygous R138*$^{stop}$/R138*$^{stop}$
Heterozygous R325/W325
Heterozygous R138/R138*$^{stop}$ Example 2

Generation of Human Induced Pluripotent Stem Cells (hiPSCs)

This example describes the generation of human iPSCs from BJ human foreskin fibroblasts. A non-infectious (non-packaging) self-replicating Venezuelan equine encephalitis (VEE) virus RNA replicon was used to express transcription factors Oct4, Klf4, Sox2, and Glis1 (VEE-OKS-iG replicon) using the Simplicon RNA Reprogramming Kit (Cat. No. SCR549 and SCR550, Millipore; Yoshioka, N. et al., 2013, Cell Stem Cell 13:246-154). VEE replicon is a positive sense-single-stranded RNA that mimics cellular RNA with a 5'cap and polyA tail. Cells are co-transduced with B18R RNA, which encodes a type 1 interferon-binding protein. Expressed B18R protein, as well as B18R protein added to the medium, suppresses the cellular interferon response.

Example 3

Immunohistochemistry to Measure Expression of Pluripotent Stem Cell Markers in hiPSCs Human iPSCs were tested for expression of pluripotent stem cell markers Oct 4, Sox2, Nanog, TRA-1-60, and TRA-1-81 using immunohistochemistry.

Cells were fixed as follows. Aspirate media from wells of 6-well tissue culture plate in which cells as in Example 1 are cultured. Wash 1× with dPBS. Aspirate dPBS. Add 2 ml of 4% PFA (paraformaldehyde) to each well. Incubate 20 minutes at room temperature. Aspirate PFA. Wash 3× with dPBS (2 minutes per wash). Leave the last wash on the cells. Store at 4° C. until ready to use.

Fixed cells were immunostained with antibodies to stem cell markers Oct 4, Sox2, Nanog, TRA-1-60, and TRA-1-81 and with DAPI for nuclear staining.

Immunohistochemistry of primed hiPSCs showed expression of Sox2 and Oct 4, both markers of pluripotency.

Example 4

Cell Culture of hiPSCs to Maintain in a Pluripotent State

Before introduction of targeting constructs into hiPSCs, it is desirable to maintain the cells in their pluripotent state. Cells can also be maintained in their pluripotent state after introduction of targeting constructs to provide cells an opportunity to recover from the transfection process and propagate before performing subsequent procedures.

hiPSCs were cultured to maintain a pluripotent state in MTESR medium from Stemcell Technologies Inc. and on a surface-coating matrix-promoting substance vitronectin or MATRIGEL matrix). MTESR medium is a complete serum-free defined formulation containing recombinant human basic FGF, and recombinant human TGFbeta. Media is changed daily.

Example 5

Differentiation of hiPSCs

In this Example a five step directed differentiation protocol adapted from D'Amour 2006, supra and Hua 2013, supra is used to differentiate hiPSCs into stem-cell derived pancreatic beta cells.

hiPSCs are dissociated using Dispase (3-5 minutes) and, subsequently, Accutase (both from Invitrogen) (5 minutes). Cells are suspended in human ES medium containing 10 µM ROCK inhibitor (Y27632) and filtered through a 70 µm cell strainer. Cells are then plated at a density of 400,000 cell per well in 12-well plates. After 1 or 2 days, when cells reach 80%-90% confluency, differentiation is started. Detailed formulations of differentiation media are listed in Figure x. Typically, cells are assayed between day 12 and day 16. For measuring proliferation rate, cells were assayed at day 12. Insulin contents are measured using the Insulin ELISA Kit (Mercodia).

Media changes/days are as follows.
Day 2: RPMI Activin A (100 ng/ml)+0.2% fetal bovine serum
Day 4: RPMI+FGF10 (50 ng/ml)+KAAD-cyclopamine (0.25 µM)+2% FBS
Day 6: DMEM+FGF10 (50 ng/ml)+KAAD-cyclopamine (0.25 µM)+retinoic acid (2 uM)+LDN193189 (250 nM)+B27
Day 9: CMRL+Exendin-4 (50 ng/ml)+SB431542 (2 uM)+B27
Day 13+: CMRL+B27

Differentiation is monitored by expression of markers OCT4 (pluripotency marker), SOX17 (definitive endoderm marker), PDX1 (primitive endgut marker), NGN3 (endocrine precursor marker) INS (endocrine marker —C-peptide and pro-insulin), and GCG (endocrine marker-glucagon), and anti-ZnT8, and anti-urocortin-3.

Differentiation is also monitored by cell morphology.

Example 6

Grafting of Stem-Cell Derived Pancreatic Beta Cells into Recipient Mice

This Example describes grafting stem-cell derived pancreatic beta cells into recipient mice using a protocol adapted from Szot, 2007, supra and Hua, 2013, supra.

On day 12 of differentiation, cells are dissociated using trypLE (5 minutes at room temperature). Aliquots of 2 to 3 million cells are collected into a 1.5 mL microcentrifuge tube. Cells are spun down, and the supernatant is discarded. 10-15 µl Matrigel (BD Biosciences) is added into each tube.

Pelleted cells are carefully aspirated off the bottom of a 1.5 mL microcentrifuge tube using a p200 pipetman and a straight, thin-wall pipette tip. A length of PE50 tubing is attached to the pipette tip using a small silicone adapter tubing. Cells are allowed to settle, in the tip, and then are transferred to the PE50 tubing by slowly dialing the pipetman. Once the cells are near the end of the PE50 tubing, a kink is made and the silicone adaptor tubing is placed over the kink. The PE50 tubing is transferred to a 15 mL conical containing a cut 5 mL pipet, and the PE50 tubing is taped over the side of the 5 mL pipet to prevent curling during centrifuging. Cells are allowed to reach 1,000 rpm and stopped.

Recipient mice are anesthetized, shaved, and cleaned. A small incision is made on the left flank of the mouse and the kidney is exposed. The kidney, fat, and tissue are kept moist with normal saline swab. The distal end of the PE50 is attached to a Hamilton screw drive syringe, containing a pipette tip, using the silicone adaptor tubing. A small nick is made on the right flank side of the kidney, not too large nor too deep. The beveled end of the PE50 tubing, nearest the cells, is carefully placed under the capsule, the tubing is moved around gently to make space while swabbing normal saline; a dry capsule can tear easily. A small air bubble is delivered under the capsule by slowly dialing the syringe screw drive. Cells are then slowly delivered behind the air bubble. Once the cells have been delivered kidney homeostasis is maintained and the nick is cauterized with low heat. The kidney is placed back into the cavity and the peritoneum and skin are sutured and stapled. Mice are immediately treated with Flunixin and Buprenorphine s.q. and placed in a cage on a heating pad.

After grafting, animals are allowed to develop for a period during which the grafted cells can undergo further differentiation to more closely resemble adult pancreatic beta cells. The period of development is at least a week, a month or at least three months. In some mice, grafted cells begin to function about two weeks after transplantation.

Three months after transplantation, human C-peptide is determined in the sera of recipient mice. An intraperitoneal glucose tolerance test performed between 100 and 120 days after transplantation.

Example 7

Measurement of Calcium Flux in Stem Cell-Derived Pancreatic Beta Cells

In this Example, calcium flux in stem cell-derived beta-pancreatic cells is measured (adapted from Pagliuca, 2014, supra). Each well of a 96-well plate is treated with a 50 µl of hESC-qualified Matrigel (BD Biosciences) that have been diluted 1:75 in DMEM:F12 (Invitrogen). The plate is incubated for 60 min in the incubator before the excess matrigel solution is aspirated off to leave a thin layer of extracellular matrix to promote cell attachment. hPSC-derived differentiated clusters (approximately 20 clusters per well) are resuspended in 100 µl of CMRL supplemented media and added to these coated wells to incubate for 24 hr.

After incubation and attachment, the wells are washed with prewarmed (37 C) Krb buffer containing 2.5 mM glucose. The clusters are then incubated with 50 mM Ca2+-sensitive fluorescent probe Fluo4-AM (Life Technologies; F14217) in 2.5 mM glucose Krb buffer for 45 min in a 37 C incubator. Clusters are washed with 2.5 mM glucose Krb buffer then incubated further in 37 C incubator for additional 15 min. Clusters are then immediately staged on an Axio-Zoom V16 microscope (Carl Zeiss) for acquisition of high resolution time series imaging.

Fluo-4 AM is illuminated at 488 nm and emission is recorded between 490 and 560 nm. Time series images are acquired at single cell resolution of 80× magnification, every 17 s. Up to 10 wells are imaged simultaneously. Progression of glucose challenges and time of the stimulation during imaging is as follows. Imaging is started with 5 min incubation in low glucose Krb containing 2 mM glucose. This is followed by a 5 min incubation in high glucose Krb containing 20 mM glucose. Sequential 5 min low and high glucose challenges are repeated two more times. Finally, wells are incubated in Krb containing 30 mM KCl as a depolarization challenge. Between the stimulations, imaging is stopped and clusters are quickly washed with 2 mM glucose Krb buffer. Then the next low or high glucose solution is added and imaging resumed. Fluorescence intensity changes during imaging are analyzed using ImageJ/Fiji by applying StackReg to correct for the movement of the clusters over the course of the imaging, and ROI manager to measure the fluorescence intensity of the cluster or cells within the cluster throughout the imaging. Analysis of the cluster is done by the measurement of the average fluorescence intensity of the whole cluster which is called population analysis or average fluorescence intensity of the individual cells within the cluster which is called single cell analysis.

Example 8

Marker Expression in Stem Cell-Derived Pancreatic Beta Cells by Immunohistochemistry In this Example, marker expression is measured in stem cell-derived beta-pancreatic cells by immunohistochemistry (adapted from Pagliuca, 2014, supra). Differentiated cell clusters are fixed by immersion in 4% PFA for 1 hr at room temperature (RT). Samples are washed 3 times with PBS, embedded in Histogel (Thermo), and sectioned at 10 mm for histological analysis. Sections are subjected to deparaffinization using Histoclear (Thermoscientific; C78-2-G) and rehydrated. For antigen retrieval slides are emerged in 0.1M EDTA (Ambion; AM9261) and placed in a pressure cooker (Proteogenix; 2100 Retriever) for two hours.

Slides are blocked with PBS+0.1% Triton X-100 (VWR; EM-9400)+5% donkey serum (Jackson Immunoresearch; 017-000-121) for 1 hr at RT, followed by incubation in blocking solution with primary antibodies overnight at 4 C. The following primary antibodies are used 1:100 unless otherwise noted: goat anti-human PDX-1/IPF1 (R&D Systems; AF2419), mouse anti-Nkx6.1 (University of Iowa, Developmental Hybridoma Bank; F55A12-supernatant) (1:100), rat anti-insulin (pro-)/C-peptide (Developmental Studies Hybridoma Bank; GN-ID4), mouse anti-glucagon (Abcam; ab82270), goat anti-somatostatin (Santa Cruz Biotechnology sc7819), guinea pig anti-insulin (Dako; A0564), anti-ZnT8, and anti-urocortin-3. Cells are washed twice in PBS the next day, followed by secondary antibody incubation for 2 hr at RT (protected from light). Secondary antibodies conjugated to Alexa Fluor 488 or 594 are used to visualize primary antibodies.

Following two washes with PBS, the histology slides are mounted in Vectashield mounting medium with DAPI (Vector Laboratories; H-1200), covered with coverslips and sealed with nail polish. Representative images are taken using an Olympus IX51 Microscope or Zeiss LSM 510 or 710 confocal microscope.

Example 9

Marker Expression in Stem Cell-Derived Pancreatic Beta Cells by Flow Cytometry

In this Example, marker expression is measured in stem cell-derived beta-pancreatic cells by flow cytometry (adapted from Pagliuca, 2014, supra). Differentiated cell clusters are dispersed into single-cell suspension by incubation in TrypLE Express (Invitrogen) at 37° C. until clusters dissociated to single cells upon mixing by pipetting gently up and down (typically 10-15 min). The TrypLE is quenched with 3-4 volumes of culture media and cells are spun down for 3 min at 1000 rpm. Cells, generally 1-2 million, are washed once in PBS (1 mL) and transferred to a 1.7 ml microcentrifuge tube (Bioscience; 11510). Cells are resuspended in 4% PFA and incubated on ice for 30 min. Cells are then washed once in PBS followed by incubation in blocking buffer (PBS+0.1% Triton X-100+5% donkey serum) on ice for 1 hr.

Cells are then resuspended in blocking buffer with primary antibodies and incubated at 4 C overnight. Primary antibodies, diluted 1:300 unless otherwise noted: Mouse anti-Nkx6.1, rat anti-insulin (pro-)/C-peptide, mouse anti-glucagon, and goat anti-somatostatin. Cells are washed twice in blocking buffer and then incubated in blocking buffer with secondary antibodies on ice for 2 hr (protected from light). Secondary antibodies conjugated to Alexa Fluor 488 or 647 (Life Technologies) are used to visualize primary antibodies. Cells are then washed 3 times in sorting buffer (PBS+0.5% BSA (Sigma; A8412) and finally resuspended in 500-700 ml sorting buffer, filtered through a 40 mm nylon mesh into flow cytometry tubes (BD Falcon; 352235), and analyzed using the LSR-II flow cytometer (BD Biosciences) with at least 30,000 events recorded. Analysis of the results is performed using FlowJo software.

Example 10

Gene Expression Analysis of Stem Cell-Derived Beta-Pancreatic Cells

In this Example, gene expression analysis is performed on stem cell-derived pancreatic beta cells (SC-b) (adapted from Pagliuca, 2014 supra). To analyze global gene expression of SC-b cells, a recently described fixation and sorting strategy is used to isolate NKX6-1+/INS+SC-b cells from the heterogeneous cell clusters (S. Hrvatin et al., 2014, Proc. Natl. Acad. Sci. 11:3038-3043). Two independent differentiation batches of SC-b clusters are harvested in single cell suspension using TrypLE and fixed in 4% PFA containing RNasin (VWR PAN2615) on ice for 30 min. Fixed cells are incubated with primary antibodies (mouse anti-NKX6-1 diluted 1:100 and guinea pig anti-insulin diluted 1:100) for 30 min in buffer containing RNasin, washed twice and then incubated with secondary antibodies (anti-mouse Alexa Fluor 488 and anti-guinea pig Alexa Fluor 647) in buffer containing RNasin for 30 min each.

After antibody staining, cells are sorted by fluorescence activated cell sorting (FACS) to obtain at least 100,000 cells per sample. Samples are subsequently incubated in Digestion Buffer (RecoverAll Total Nucleic Acid Isolation Kit, Ambion AM1975) at 50° C. for 3 hr, prior to RNA isolation according to manufacturer's instructions. RNA concentration is quantified using Nanodrop 1000. Double-stranded cDNA is generated by reverse transcription from at least 100 ng of total RNA according to manufacturer's instructions (Illumina TotalPrep RNA Amplification Kit, Life Technologies, AMIL1791). At least 750 ng cRNA per sample is hybridized to Human HT-12 Expression BeadChips (Illumina) using the Whole-Genome Expression Direct Hybridization kit (Illumina). Chips are scanned on the Illumina Beadstation 500. Raw data are adjusted by background subtraction and rank-invariant normalization (GenomeStudio software, Illumina). Before calculating fold change, an offset of 20 is added to all probe set means to eliminate negative signals. The p-values for differences between mean signals are calculated in GenomeStudio by t test and corrected for multiple hypotheses testing by the Benjamini-Hochberg method in combination with the Illumina custom false discovery rate (FDR) model. These SC-b cell microarray data and the previously published hPSC, PH, fetal b and adult b cell data (Hrvatin et al., 2014) are imported into the R statistical computing platform using the programming packages lumi and EMA. Samples are analyzed by hierarchical clustering using Pearson's correlation and Ward linkage. The pattern of clustering is robust to other distance and linkage metrics.

Example 11

Analysis of Stem Cell-Derived Beta-Pancreatic Cells by Electron Microscopy

In this Example, stem cell-derived beta-pancreatic cells are analyzed by electron microscopy (adapted from Pagliuca, 2014, supra). To analyze granular ultrastructure, differentiated clusters are fixed at room temperature for 2 hr with a mixture containing 1.25% PFA, 2.5% glutaraldehyde, and 0.03% picric acid in 0.1 M sodium cacodylate buffer (pH 7.4). Samples are then washed in 0.1 M cacodylate buffer and postfixed at room temperature for at least 2 hr with a mixture of 1% Osmium tetroxide (OsO4) and 1.5% Potassium ferrocyanide (KFeCN6). Next samples are washed in 0.1M cacodylate buffer and postfixed with 1% Osmiumtetroxide (OsO4)/1.5% Potassiumferrocyanide (KFeCN6) for 1 hr. After washing three times with water, samples are stained in 1% aqueous uranyl acetate for 1 hr, washed twice in water and subsequently dehydrated in grades of alcohol (10 min each; 50%, 70%, 90%, 2×10 min 100%). A one hour incubation in propyleneoxide is followed by infiltration overnight in a 1:1 mixture of propyleneoxide and TAAB Epon (Marivac Canada, St. Laurent, Canada). After the overnight infiltration, TAAB Epon is used to embed the samples and they are polymerized at 60 C for 48 hr. Sample sections are cut ultrathin (approximately 60 nm) on a Reichert Ultracut-S microtome and placed onto copper grids. These are then stained with 0.2% lead citrate. A JEOL 1200EX Transmission electron microscope or a TecnaiG2 Spirit BioTWIN is used to analyze the samples. Images from at least two independent different batches for each protocol are recorded with an AMT 2k CCD camera. ImageJ software is used to analyze and quantify images.

For determination of granular protein composition, immunogold labeling is performed on differentiated clusters. Samples are washed with PBS and then placed into 0.5 mM EDTA in PBS. A 200 ml cushion of 8% paraformaldehyde (in 0.1 M Sodium Phosphate buffer, pH 7.4) is then layered with 800 ml of sample. The samples are pelleted for 3 min at 3000 rpm then placed into 4% paraformaldehyde for 2 hr at room temperature. Cell pellets are then washed with PBS and treated with 2.3 M sucrose and 0.2 M glycin in PBS for 15 min, then placed into liquid nitrogen prior to being sectioned at −120° C. Sections are then transferred to formvar-carbon coated copper grids are stored at 4° C. in PBS or 2% gelatin until immunogold labeling is performed. The gold labeling process is performed at room temperature on a piece of parafilm. The following primary antibodies are used: 1:500 mouse anti-glucagon (Abcam; ab82270) and guinea pig anti-insulin (Dako; A0564). Primary antibody and protein-A gold are first diluted in 1% BSA in PBS, before staining. The diluted antibody solution is centrifuged for 1 min at 14000 rpm. Sample grids are blocked with 1% BSA for 10 min then incubated in 5 ml drops of primary antibody solution for 30 min. The grids are then washed in 4 drops of PBS for 15 min, then incubated with 5 ml drops of 5 nm or 15 nm protein-A gold for 20 min, labeling insulin and glucagon, respectively. Protein-A labeled samples are then washed in 4 drops of PBS for 15 min and then 6 drops of double distilled water. Labeled grids are then contrasted and embedded in 0.3% uranyl acetate in 2% methyl cellulose for 10 min. Grids are picked up with metal loops then examined in a JEOL 1200EX Trans or a TecnaiG2 Spirit BioTWIN mission electron microscope. Images from at least two independent different batches are recorded with an AMT 2k CCD camera.

Example 12

Glucose Challenge Test in Mice with Grafted Differentiated Cells

In this Example, mice with grafted differentiated cells undergo a glucose challenge test (adapted from Pagliuca, 2014, supra). After two weeks of recovery from surgery, animals are analyzed by performing a glucose challenge and collecting serum for human insulin concentration measurement.

After fasting the mice for 16 hr overnight, the glucose challenge is performed by intraperitoneal (IP) injection of 2 g D-(+)-glucose/1 kg body weight and blood is collected at 30 min post glucose injection through facial vein puncture using a lancet (Feather; 2017-01). For a subset of animals, serum is collected both preinjection and 30 min postinjection in order to measure glucose responsiveness of the human insulin producing cells in vivo. Serum is separated out using Microvettes (Sarstedt 16.443.100) and stored at −80° C. until ELISA analysis. Serum human insulin levels are quantified using the Human Ultrasensitive Insulin ELISA. Kidneys containing the grafts are dissected from the mice, fixed in 4% PFA overnight, embedded in paraffin, and sectioned for histological analysis. Immunohistochemistry analysis is performed as described above.

Example 13

Glucose-Stimulated Insulin Secretion in Stem Cell-Derived Pancreatic Beta Cells

In this Example, glucose-stimulated insulin secretion is measured in stem cell-derived pancreatic beta cells (adapted from Pagliuca, 2014, supra).

Krebs buffer (Krb) is prepared as follows: 128 mM NaCl, 5 mM KCl, 2.7 mM $CaCl_2$, 1.2 mM $MgCl_2$, 1 mM $Na_2HPO_4$, 1.2 mM $KH_2PO_4$, 5 mM $NaHCO_3$, 10 mM HEPES (Life Technologies; 15630080), 0.1% BSA (Proliant; 68700) in deionized water. Krb solutions containing 2 mM glucose (low glucose), 20 mM glucose (high glucose), or 2 mM glucose and 30 mM KCl (KCl polarization challenge) are prepared and equilibrated to 37° C.

Differentiated SC-b cells (approximately 500,000 cells sampled from cultures between days 28-35 of differentiation) are sampled. These clusters (stem cell-derived cells) are washed twice with 1 ml Krb buffer and then preincubated in 3 ml low glucose Krb for two hours to remove residual insulin. Note: for all incubations tube lids are left open and covered by a lid that allowed for air exchange. Clusters are washed 2 times in Krb and then incubated in 1 ml low glucose Krb for 30 min. A sample of 200 µl of the supernatant is collected after incubation for ELISA analysis (low glucose sample). Clusters are washed 2 times in Krb and then incubated in high glucose Krb for 30 min and 200 µl of supernatant is collected after incubation (high glucose sample). Challenging with low and high glucose is repeated two additional times (3 paired challenges in total for each differentiation batch). Finally, clusters are washed twice in Krb and then incubated in Krb containing 2 mM glucose and 30 mM KCl (polarization challenge) for 30 min. A sample of 200 µl of the supernatant is collected after incubation for ELISA analysis (KCl polarization challenge sample). After the KCl challenge, clusters are dispersed into single cells using TrypLE Express (Life Technologies; 12604-013) and cell number is counted automatically by a Vi-Cell (Beckman Coulter).

Supernatant samples containing secreted insulin are processed using the Human Ultrasensitive Insulin ELISA (ALPCO Diagnostics; 80-INSHUU-E01.1) and samples are measured by a FLUOstar optima spectrophotometer (BMG lantech) at 450 nm. If the ELISA is not performed on the same day, samples are stored at −80 C. Insulin concentrations in samples collected for each challenge are normalized by the cell number in each sample, as measured by the Vi-Cell automated counting.

Proinsulin and Insulin Content Measurements

Collected cells are settled to the bottom of a tube and the supernatant removed. The cell pellets are placed in 1 ml of 1.5% HCl in 70% ethanol and stored at −20° C. for 24 hr. Cell pellets are then vortexed briefly and stored at −20° C. for an additional 24 hr. Tubes are then centrifuged at 2100 RCF for 15 min. The 1 ml supernatant is then transferred to a new tube and neutralized by addition of 1 ml of 1M TRIS (pH 7.5). The neutralized supernatant containing the extracted proinsulin and insulin is then measured using intact human proinsulin (BioVendor; RZ193094100) and human Ultrasensitive Insulin ELISA kits.

Example 14

C-Peptide Release and Content Assay in Stem Cell-Derived Pancreatic Beta Cells

In this Example, the C-peptide release and content assay is performed as described previously (Sakano D. et al., 2014, Nat. Chem. Biol. 10:141-148) with minor modifications (adapted from Shahjalal, 2014, supra). Briefly, differentiated cells at the end of stage 5 are preincubated at 37° C. for 30 min with DMEM (Life Technologies) containing minimal essential medium, 1% B27 supplement, and 2.5 mM glucose. Cells are washed twice with PBS and then incubated at 37° C. for 1 hr with DMEM containing 2.5 mM glucose at 100 µl per well. The culture medium is collected, and the same cells are further incubated with DMEM containing 20 mM glucose or DMEM containing 2.5 mM glucose supplemented with various stimulants, i.e., 2 µM (−)-Bay K8644 (Sigma-Aldrich), 100 µM tolbutamide (Wako), 250 µM carbachol (Sigma-Aldrich), 0.5 mM IBMX, or 30 mM potassium chloride (KCl) (Wako), at 37° C. for another 1 h. The culture media are collected and stored at −20° C. until analysis. Next, the cells are lysed with lysis buffer (0.1% Triton X-100 in PBS) supplemented with 1% protease inhibitor cocktail (Nacalai Tesque). C-peptide secretion into the culture media and C-peptide content of the cell lysates are measured using the human C-peptide ELISA Kit (ALPCO Diagnostics). The amount of C-peptide is normalized to the amount of total protein in the corresponding cell lysate.

Although the invention has been described in detail for purposes of clarity of understanding, certain modifications may be practiced within the scope of the appended claims. All publications (including GenBank Accession numbers, UniProtKB/Swiss-Prot accession numbers and the like), patents and patent applications cited are herein incorporated by reference in their entirety for all purposes to the same extent as if each individual publication, patent and patent application was specifically and individually indicated to be incorporated by reference in its entirety for all purposes. In the event of any variance in sequences associated with GenBank and UniProtKB/Swiss-Prot accession numbers and the like or in website, or disease criteria of an organization, the application refers to those in effect on its effective filing date. Unless otherwise apparent from the context any embodiments, elements, features, steps or the like can be used in combination with each other.

What is claimed is:

1. A cell culture comprising:
   i) a population of human induced pluripotent stem cells (hiPSCs);
   ii) a surface coating matrix; and
   iii) serum-free, defined culture medium comprising recombinant human basic FGF, and recombinant human TGFβ;
   wherein each hiPSC comprises in its genome a heterozygous or homozygous R325W allele of the human SLC30A8 gene, and wherein culturing of the hiPSCs on the surface coating matrix and in the culture medium maintains the hiPSCs in a pluripotent state.

2. The cell culture of claim 1, wherein each hiPSC comprises in its genome a homozygous R325W allele of the human SLC30A8 gene.

3. The cell culture of claim 1, wherein each hiPSC comprises in its genome a heterozygous R325W allele of the human SLC30A8 gene.

4. The cell culture of claim 1 wherein the hiPSCs are a clonal cell line.

5. The cell culture of claim 1, wherein the hiPSCs are generated by homologous recombination with a gene targeting construct comprising a sequence encoding R325W, wherein the sequence is flanked by homology arms; wherein the recombination is enhanced by CRISPR/Cas9-mediated cleavage between segments of the endogenous hiPSC genome homologous to the homology arms.

6. The cell culture of claim 5, wherein the gene targeting construct is a single-stranded donor oligonucleotide.

7. A cell culture comprising:
   i) a population of human induced pluripotent stem cells (hiPSCs);
   ii) a surface coating matrix; and
   iii) a serum-free, defined culture medium comprising recombinant human basic FGF, and recombinant human TGFβ;
   wherein each hiPSC comprises in its genome a heterozygous or homozygous R138*$^{stop}$ allele of the human SLC30A8 gene, and wherein culturing of the hiPSCs on the surface coating matrix and in the culture medium maintains the hiPSCs in a pluripotent state.

8. The cell culture of claim 7, wherein each hiPSC comprises in its genome a homozygous R138*$^{stop}$ allele of the human SLC30A8 gene.

9. The cell culture of claim 7, wherein each hiPSC comprises in its genome a heterozygous R138*$^{stop}$ allele of the human SLC30A8 gene.

10. The cell culture of claim 7, wherein the hiPSCs are a clonal cell line.

11. The cell culture of claim 7, wherein the hiPSCs are generated by homologous recombination with a gene targeting construct comprising a sequence encoding R138*$^{stop}$, wherein the sequence is flanked by homology arms; wherein the recombination is enhanced by CRISPR/Cas9-mediated cleavage between segments of the endogenous hiPSC genome homologous to the homology arms.

12. The cell culture of claim 11, wherein the gene targeting construct is a single-stranded donor oligonucleotide.

\* \* \* \* \*